(12) United States Patent
Nagy et al.

(10) Patent No.: US 9,422,380 B2
(45) Date of Patent: Aug. 23, 2016

(54) NON-BRIDGED METALLOCENE COMPLEXES FOR THE POLYMERIZATION OF OLEFINS

(71) Applicant: Basell Polyoefine GmbH, Wesseling (DE)

(72) Inventors: Sandor Nagy, Webster, TX (US); Shahram Mihan, Bad Soden (DE); Ilya E. Nifant'ev, Moscow (RU); Pavel V. Ivchenko, Moscow (RU); Vladimir V. Bagrov, Moscow (RU); Igor A. Kashulin, Moscow (RU)

(73) Assignee: Basell Polyolefine Wesseling (DE)

( * ) Notice: Subject to any disclaimer, the term of this patent is extended or adjusted under 35 U.S.C. 154(b) by 0 days.

(21) Appl. No.: 14/677,668

(22) Filed: Apr. 2, 2015

(65) Prior Publication Data

US 2015/0284489 A1   Oct. 8, 2015

Related U.S. Application Data

(60) Provisional application No. 61/974,790, filed on Apr. 3, 2014.

(51) Int. Cl.
C08F 4/6592 (2006.01)
C08F 10/00 (2006.01)
C08F 210/16 (2006.01)
C07F 17/00 (2006.01)
C08F 4/659 (2006.01)

(52) U.S. Cl.
CPC ............... C08F 210/16 (2013.01); C07F 17/00 (2013.01); C08F 4/65925 (2013.01); C08F 4/65912 (2013.01); C08F 4/65916 (2013.01); C08F 10/00 (2013.01)

(58) Field of Classification Search
CPC ............. C08F 4/65912; C08F 4/65916; C08F 4/65923; C08F 10/00; C08F 4/65925; C08F 210/16

See application file for complete search history.

(56) References Cited

U.S. PATENT DOCUMENTS 4,808,561 A * 2/1989 Welborn, Jr. ............ C08F 10/00
502/103

* cited by examiner

*Primary Examiner* — Caixia Lu

(57) ABSTRACT

The present disclosure relates to metallocene catalyst and the use thereof to make polyolefins. In particular, the present disclosure relates to silyl-functionalized metallocene catalyst and the use of the silyl-functionalized metallocene catalyst to polymerize olefins and yield a polyolefin. Also, the present disclosure relates to a method for producing a polyolefin comprising at least the step of contacting an olefin with a metallocene catalyst to produce a polyolefin. In particular, the present disclosure provides a method for producing a polyolefin comprising the step of contacting an olefin with a silyl-functionalized metallocene catalyst.

13 Claims, 2 Drawing Sheets

NON-BRIDGED METALLOCENE COMPLEXES FOR THE POLYMERIZATION OF OLEFINS

CROSS-REFERENCE TO RELATED APPLICATIONS

This application claims the benefit of priority under 35 U.S.C. §119(e) of U.S. Provisional Application No. 61/974,790 filed Apr. 3, 2014, the contents of which are incorporated herein by reference in their entirety.

TECHNICAL FIELD

In general, the present disclosure relates to the field of chemistry. More specifically, the present disclosure relates to non-bridged metallocene complexes which may be used in the polymerization of olefins.

BACKGROUND

There exists a constant search to develop new olefin polymerization catalysts, catalyst activation processes, and methods of making and using catalysts. Mono-1-olefins (α-olefins), including ethylene, can be polymerized with catalyst compositions employing titanium, zirconium, vanadium, chromium or other metals, impregnated on a variety of support materials, often in the presence of cocatalysts. These catalyst compositions may be useful for both homopolymerization of ethylene, as well as copolymerization of ethylene with co-monomers such as propylene, 1-butene, 1-hexene, or other higher alpha-olefins.

SUMMARY

In general, the present disclosure provides catalyst compositions, methods and systems for preparing non-bridged metallocene catalysts. Additionally, the present disclosure provides non-bridged metallocene catalyst compositions that may be used to polymerize olefins. More specifically, the metallocene catalyst compositions disclosed herein may be used in polymerization reactions, methods for polymerizing olefins. In specific embodiments, the catalyst compositions as disclosed herein may be used to form ethylene polymers and copolymers of α-olefins.

In specific embodiments, the present disclosure provides catalyst compositions comprising a silyl functionalized metallocene compound. In additional embodiments, the catalyst composition may include an organoaluminum compound. In some embodiments, the catalyst composition is supported on at least one solid oxide support compound.

In some aspects, the present disclosure provides a method of producing a polyolefin polymer. In some embodiments, the resulting polymer contains at least a bimodal distribution of average molecular weight polymers. In general, the method for producing the polymer includes the steps of: a) immobilizing a metallocene catalyst on a solid support; b) optionally, contacting a metallocene catalyst composition with an activator in a manner which activates 10% to 90% of the supported metallocene catalyst composition to form a first activated catalyst. In some embodiments, the activator is an aluminoxane defined by either of the following formulas:

 (Formula I) or

 (Formula II)

wherein: each R is independently alkyl$_{C\leq6}$; x is 3-50; and y is 1-50; and the molar ratio of aluminum of the aluminoxane to the metal of the metallocene catalyst is from 25-1000, more preferably 50-500; c) optionally, contacting the metallocene catalyst with an activator in a manner which activates 10% to 90% of the metallocene catalyst to form a second activated catalyst, wherein the activator is an aluminoxane defined by either of the following formulas:

 (Formula III) or

 (Formula IV)

wherein: each R' is independently alkyl$_{C\leq6}$; x' is 3-50; and y' is 1-50; and the molar ratio of aluminum of the aluminoxane to the metal of the metallocene catalyst is from 50 to 500; or a borate compound,

 (Formula V)

wherein: X" is 3 or 4; wherein: when X" is 4, then the compound is negatively charged and further comprises a cation, Y"; wherein: Y" is triphenylmethylium or dimethylanilinium; or a borate compound,

 (Formula VI)

wherein: $X_1$, $X_2$, and $X_3$ are each independently hydroxy, alkyl$_{(C\leq12)}$, aryl$_{(C\leq12)}$, haloalkyl$_{(C\leq12)}$, or haloaryl$_{(C\leq12)}$; d) contacting the first activated catalyst and/or the second activated catalyst with a terminal alkene$_{(C2-8)}$ under conditions suitable to for polymerizing the terminal alkene$_{(C2-8)}$ into a polyolefin, wherein the polyolefin exhibits a bimodal average molecular weight distribution, wherein the average molecular weight distribution at the first mode is from 200,000 to 750,000 Daltons as measured by gel permeation chromatography (GPC), and the molecular weight distribution at the second mode is from 100,000 to 750,000 Daltons as measured by GPC. In some embodiments, the metallocene catalyst is a compound defined by the formula:

In some embodiments, the catalyst composition comprises a catalyst having the formula:

 (Formula VII)

wherein: $L_1$ and $L_2$ are each independently a compound of the formula:

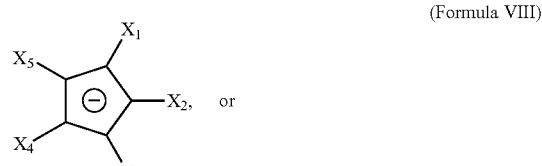 (Formula VIII)

or

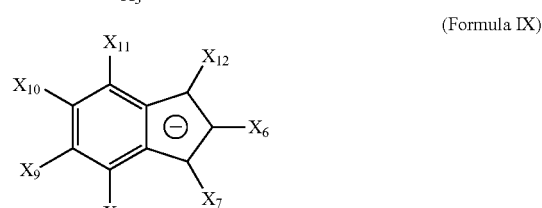 (Formula IX)

wherein: $X_1$ is hydrogen, alkyl$_{C\leq6}$, or alkenyl$_{C\leq6}$; and $X_2$, $X_3$, $X_4$, $X_5$, $X_6$, $X_7$, $X_8$, $X_{10}$, and $X_{11}$ are each independently hydrogen, alkyl$_{C\leq8}$, alkenyl$_{C\leq8}$, alkynyl$_{C\leq8}$, aryl$_{C\leq12}$, aralkyl$_{C\leq12}$, heterocycloalkyl$_{C\leq12}$, or heteroaryl$_{C\leq12}$; $X_9$ is hydrogen, alkyl$_{C\leq8}$, alkenyl$_{C\leq6}$, or —O—Si—R$^1$R$^2$R$^3$, wherein R$^1$, R$^2$ and R$^3$ are independently selected from alkyl$_{C\leq6}$, or alkenyl$_{C\leq6}$; $X_{12}$ is hydrogen, alkyl$_{C\leq8}$, or alkenyl$_{C\leq6}$; M is a transition metal of Group 4; and $Y_1$ and $Y_2$ are each independently a hydride, halide, carboxylate, phosphine, amine, alkylamino, alkenylamino, alkynylamino, arylamino, aralkylamino, alkoxylate, alkenyloxylate, alkynyloxylate, aryloxylate, or aralkyloxylate.

In some embodiments, $L_1$ and $L_2$ are each independently a compound of the formula:

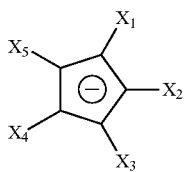

(Formula VIII)

wherein: $X_1$ is alkyl$_{C\leq6}$, alkenyl$_{C\leq6}$, a silyl substituted alkyl$_{C\leq6}$, or a silyl substituted alkenyl$_{C\leq6}$, —CH$_2$—CH$_2$—CH$_2$—SiCH$_3$Cl$_2$, —CH$_2$—CH$_2$—CH$_2$—SiCl$_3$, —CH$_2$—CH$_2$—CH$_2$—CH$_2$—CH$_2$—SiCH$_3$Cl$_2$, and $X_2$, $X_3$, $X_4$, and $X_5$ are each independently hydrogen, alkyl$_{C\leq8}$, alkenyl$_{C\leq8}$, alkynyl$_{C\leq8}$, aryl$_{C\leq12}$, aralkyl$_{C\leq12}$, heterocycloalkyl$_{C\leq12}$, heteroaryl$_{C\leq12}$, or a substituted version of any of these groups; M is a transition metal of Group 4; and $Y_1$ and $Y_2$ are each independently a hydride, halide, carboxylate, phosphine, amine, alkylamino, alkenylamino, alkynylamino, arylamino, aralkylamino, alkoxylate, alkenyloxylate, alkynyloxylate, aryloxylate, aralkyloxylate, or a substituted version of any of these groups.

In some embodiments, $L_1$ and $L_2$ are each independently a ligand of the formula:

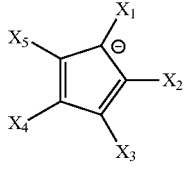

(Formula VIII)

wherein: $X_1$ is —CH$_2$—CH$_2$—CH$_2$—SiCH$_3$Cl$_2$, —CH$_2$—CH$_2$—CH$_2$—SiCl$_3$, —CH$_2$—CH$_2$—CH$_2$—CH$_2$—CH$_2$—SiCH$_3$Cl$_2$, and $X_2$, $X_3$, $X_4$, and $X_5$ are each independently hydrogen, alkyl$_{C\leq8}$, alkenyl$_{C\leq8}$, alkynyl$_{C\leq8}$, aryl$_{C\leq12}$, aralkyl$_{C\leq12}$, heterocycloalkyl$_{C\leq12}$, heteroaryl$_{C\leq12}$, or a substituted version of any of these groups; M is a transition metal of Group 4; and $Y_1$ and $Y_2$ are each independently a hydride, halide, carboxylate, phosphine, amine, alkylamino, alkenylamino, alkynylamino, arylamino, aralkylamino, alkoxylate, alkenyloxylate, alkynyloxylate, aryloxylate, aralkyloxylate, or a substituted version of any of these groups. In additional embodiments, $X_2$, $X_3$, $X_4$, and $X_5$ are hydrogen.

In some embodiments, $L_1$ and $L_2$ are each independently a compound of the formula:

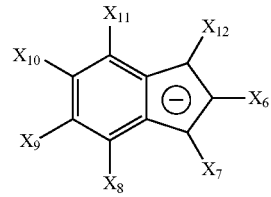

(Formula IX)

wherein: $X_6$, $X_7$, $X_8$, $X_{10}$, and $X_{11}$ are each independently hydrogen, alkyl$_{C\leq8}$, alkenyl$_{C\leq8}$, alkynyl$_{C\leq8}$, aryl$_{C\leq12}$, aralkyl$_{C\leq12}$, heterocycloalkyl$_{C\leq12}$, heteroaryl$_{C\leq12}$, or a substituted version of any of these groups; $X_9$ is hydrogen, alkyl$_{C\leq8}$, alkenyl$_{C\leq6}$, —O—Si—R$^1$R$^2$R$^3$ or a substituted version of either of these groups, wherein R$^1$, R$^2$ and R$^3$ are independently selected from alkyl$_{C\leq6}$, alkenyl$_{C\leq6}$, or a substituted version of either of these groups; $X_{12}$ is hydrogen, alkyl$_{C\leq8}$, alkenyl$_{C\leq6}$ or a substituted version of either of these groups; M is a transition metal of Group 4; and $Y_1$ and $Y_2$ are each independently a hydride, halide, carboxylate, phosphine, amine, alkylamino, alkenylamino, alkynylamino, arylamino, aralkylamino, alkoxylate, alkenyloxylate, alkynyloxylate, aryloxylate, aralkyloxylate, or a substituted version of any of these groups.

In some embodiments, $L_1$ and $L_2$ are each independently a compound of the formula:

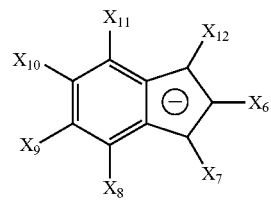

(Formula IX)

wherein: $X_6$, $X_7$, $X_8$, $X_{10}$, and $X_{11}$ are each independently hydrogen or methyl. In some embodiments, $X_9$ is hydrogen, —O—Si—R$^1$R$^2$R$^3$, wherein R$^1$, R$^2$ and R$^3$ are independently selected from methyl, tert-butyl, —CH$_2$—CH$_2$—CH$_2$—CH$_2$—CH=CH$_2$. In some embodiments, $X_{12}$ is hydrogen or —CH$_2$—CH$_2$—CH$_2$—SiCH$_3$Cl$_2$.

In some embodiments, $L_1$ and $L_2$ are each independently selected from:

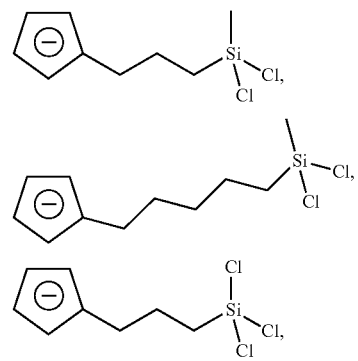

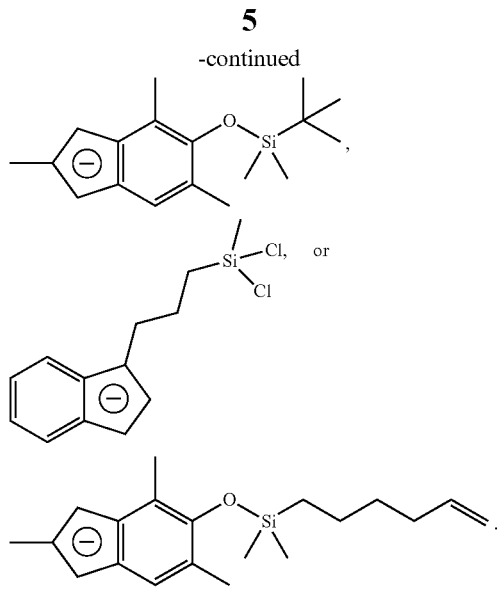

In some embodiments, M is Ti, Zr, or Hf. In some embodiments, M is Zr. In some embodiments, $Y_1$ and $Y_2$ are each independently halide. In some embodiments, $Y_1$ and $Y_2$ are each independently chloride. In some embodiments, the formula is further defined as:

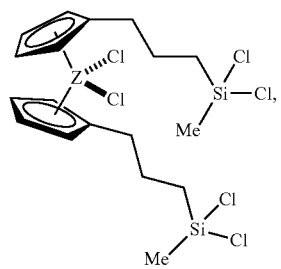

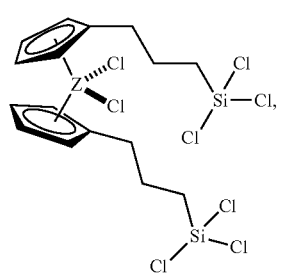

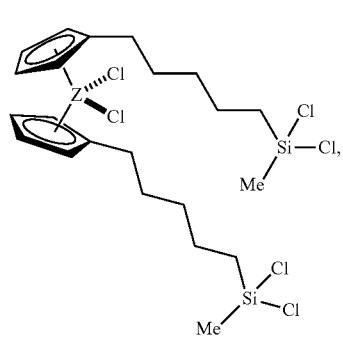

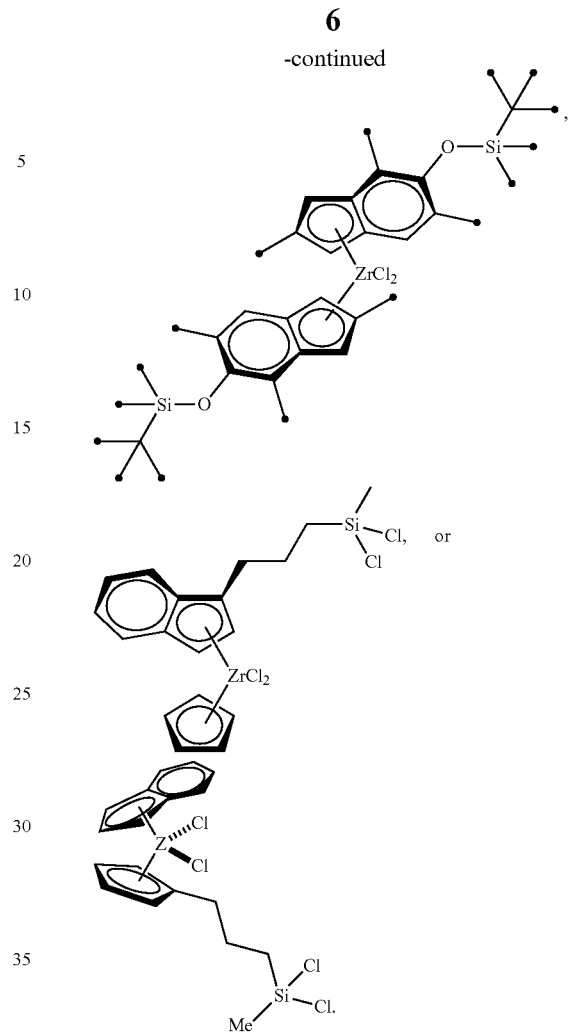

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula does not mean that it cannot also belong to another generic formula.

BRIEF DESCRIPTION OF THE DRAWINGS

The following drawings form part of the present specification and are included to further demonstrate certain aspects of the present disclosure. The disclosure may be better understood by reference to one of these drawings in combination with the detailed description of specific embodiments presented herein.

Figure 1:
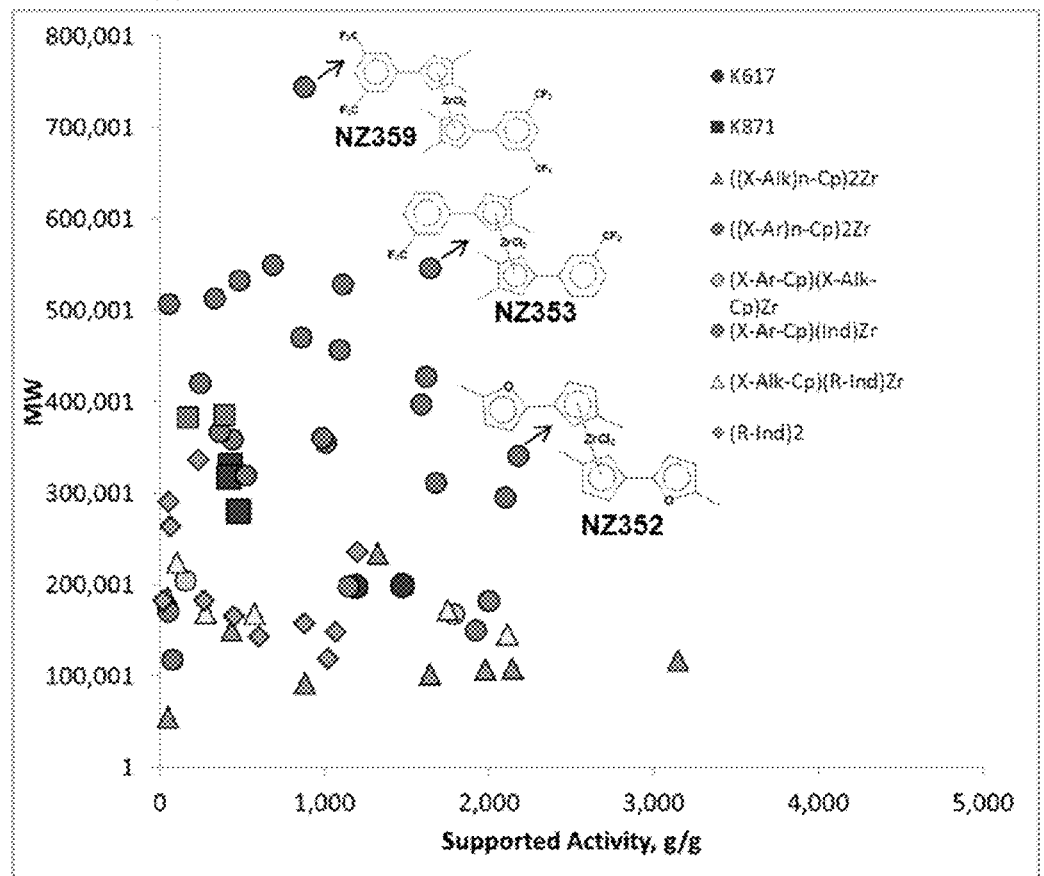
FIG. 1—Plot of the supported activity of the catalyst as a function of the molecular weight of the resultant polymer for the metallocene catalysts of Table 1. See Table 2 for the data used to generate the plot of FIG. 1.
Figure 2:
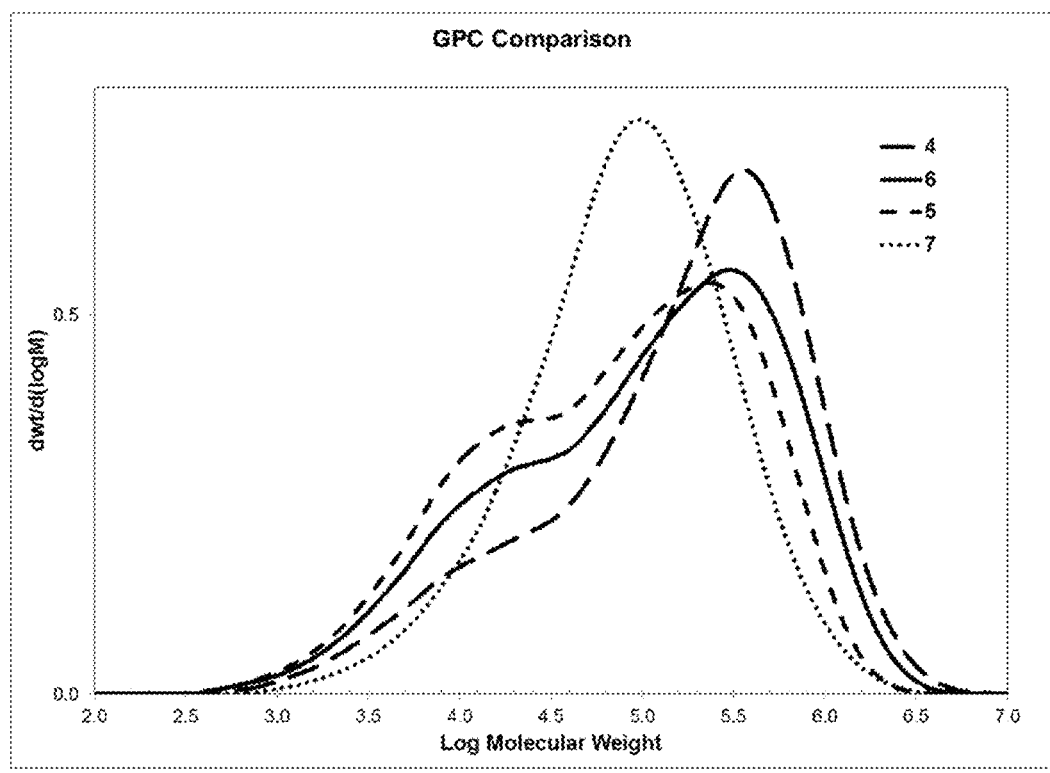
FIG. 2—Comparison of the log of the molecular weight of different activation methods.

It should be understood that the various embodiments are not limited to the arrangements and instrumentality shown in the drawings.

DETAILED DESCRIPTION OF THE INVENTION

Organometallic Catalytic Complexes

In some aspects, the present disclosure provides metallocene-type catalysts that may be used, for example, for the preparation of higher molecular weight olefin polymers without or with few branching points. In some embodiments, the olefin monomers that are used as substrates in the polymerization reactions catalyzed by the catalysts described herein include ethylene, propylene, and other 1-alkenes. In some embodiments, the catalysts comprise Group 4 metal atoms, for example, zirconium or hafnium.

Table 1 identifies catalysts and catalyst precursors discussed herein, including the compounds provided, as well as comparison compounds that are compared herein. The compounds listed in Table 1 correspond to the following formula:

TABLE 1

Metallocene Polymerization Catalysts

| Run # | M | $L_1$ | $L_2$ |
|---|---|---|---|

"Benchmarks"

| 1 | Zr | | |
| 2 | Zr | | |
| 3 | Hf | | |
| 4 | Hf | | |
| 5 | Hf | | |

$(R\text{-Alk-Cp})_2$

| 6 | Zr | | |
| 7 | Zr | | |
| 8 | Zr | | |

TABLE 1-continued
Metallocene Polymerization Catalysts
| Run # | M | L₁ | L₂ |
|---|---|---|---|
| 9 | Zr | 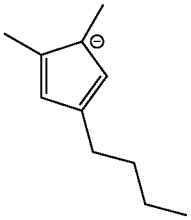 | 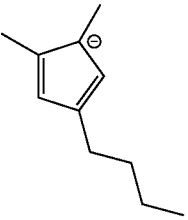 |
| 10 | Zr | 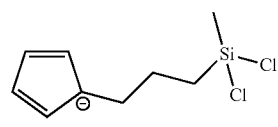 | 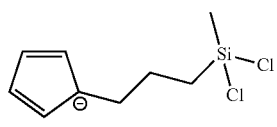 |
| 11 | Zr | 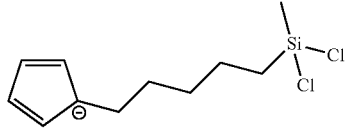 | 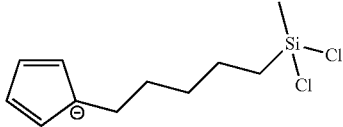 |
| 12 | Zr | 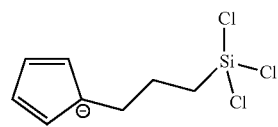 | 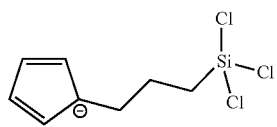 |
| 13 | Zr | 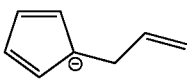 | 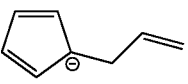 |
| 14 | Zr | 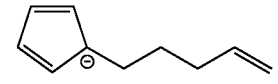 | 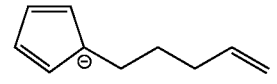 |
| 15 | Zr | 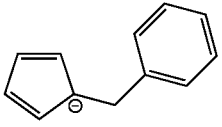 | 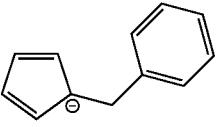 |
| 16 | Zr | 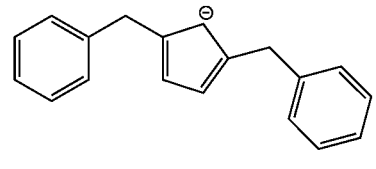 | 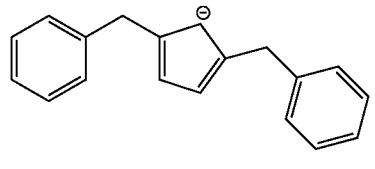 |
| 17 | Hf | 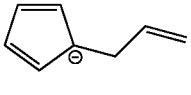 | 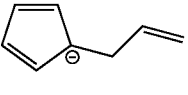 |
| 18 | Hf | 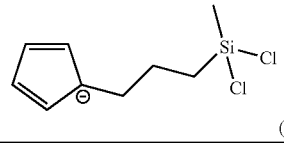 | 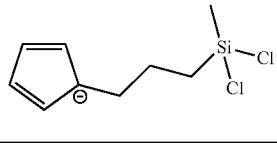 |
(R-Alk-Cp)(Ind)
| 19 | Zr |  | 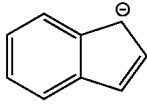 |

TABLE 1-continued
Metallocene Polymerization Catalysts
| Run # | M | L₁ | L₂ |
|---|---|---|---|
| 20 | Zr |  | 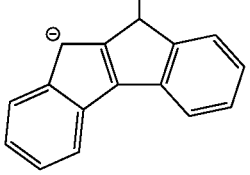 |
| 21 | Zr |  | 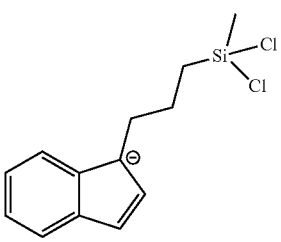 |
| 22 | Zr | 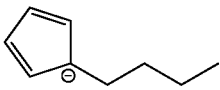 | 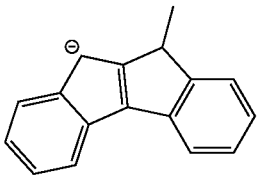 |
| 23 | Zr | 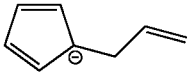 | 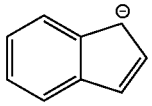 |
| 24 | Zr | 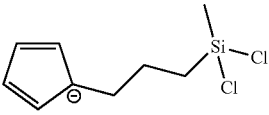 | 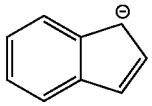 |
| 25 | Zr | 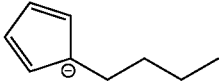 | 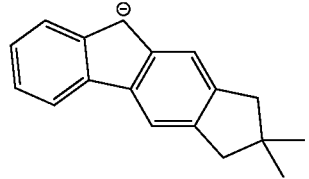 |
| 26 | Zr |  | 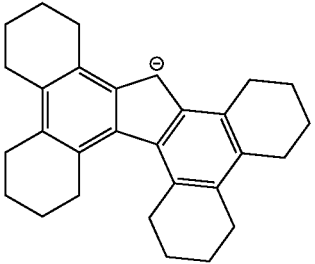 |
| | | (Ind)₂ | |
| 27 | Zr | 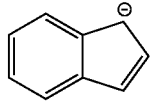 | 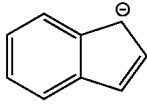 |

TABLE 1-continued

Metallocene Polymerization Catalysts

| Run # | M | L₁ | L₂ |
|---|---|---|---|
| 28 | Zr | | |
| 29 | Zr | | |
| 30 | Zr | | |
| 31 | Zr | | |
| 32 | Zr | | |
| 33 | Zr | | |
| 34 | Zr | | |
| 35 | Zr | | |
| 36 | Zr | | |

TABLE 1-continued

Metallocene Polymerization Catalysts

| Run # | M | L₁ | L₂ |
|---|---|---|---|
| 37 | Zr | indenyl anion | 4,7-dimethyl-5-(tert-butyldimethylsilyloxy)indenyl anion |
| 38 | Zr | indenyl anion | 2,4,7-trimethyl-5-(hex-5-enyldimethylsilyloxy)indenyl anion |

(Ar-Cp)₂

| Run # | M | L₁ | L₂ |
|---|---|---|---|
| 39 | Zr | 2,5-diphenylcyclopentadienyl anion | 2,5-diphenylcyclopentadienyl anion |
| 40 | Zr | 2-phenyl-5-(2-naphthyl)cyclopentadienyl anion | 2-phenyl-5-(2-naphthyl)cyclopentadienyl anion |
| 41 | Zr | 2-methyl-5-phenylcyclopentadienyl anion | 2-methyl-5-phenylcyclopentadienyl anion |
| 42 | Zr | 2-(5-methylthien-2-yl)-5-phenylcyclopentadienyl anion | 2-(5-methylthien-2-yl)-5-phenylcyclopentadienyl anion |
| 43 | Zr | 3-methyl-1-(4-methylphenyl)cyclopentadienyl anion | 3-methyl-1-(4-methylphenyl)cyclopentadienyl anion |
| 44 | Zr | 3-methyl-1-(4-chlorophenyl)cyclopentadienyl anion | 3-methyl-1-(4-chlorophenyl)cyclopentadienyl anion |
| 45 | Zr | 3-methyl-1-(4-tert-butylphenyl)cyclopentadienyl anion | 3-methyl-1-(4-tert-butylphenyl)cyclopentadienyl anion |
| 46 | Zr | 3,4-dimethyl-1-phenylcyclopentadienyl anion | 3,4-dimethyl-1-phenylcyclopentadienyl anion |
| 47 | Zr | 3,4-dimethyl-2-phenylcyclopentadienyl anion | 3,4-dimethyl-2-phenylcyclopentadienyl anion |

TABLE 1-continued

Metallocene Polymerization Catalysts

| Run # | M | L₁ | L₂ |
|---|---|---|---|
| 48 | Zr | methylcyclopentadienyl-(4-fluorophenyl) | methylcyclopentadienyl-(4-fluorophenyl) |
| 49 | Zr | methylcyclopentadienyl-(3,5-dimethyl-4-methoxyphenyl) | methylcyclopentadienyl-(3,5-dimethyl-4-methoxyphenyl) |
| 50 | Zr | dimethylcyclopentadienyl-(5-methylfuran-2-yl) | dimethylcyclopentadienyl-(5-methylfuran-2-yl) |
| 51 | Zr | 2-phenyl-5-(4-fluorophenyl)cyclopentadienyl | 2-phenyl-5-(4-fluorophenyl)cyclopentadienyl |
| 52 | Zr | methylcyclopentadienyl-(5-methylfuran-2-yl) | methylcyclopentadienyl-(5-methylfuran-2-yl) |
| 53 | Zr | methylcyclopentadienyl-(5-methylfuran-2-yl) | methylcyclopentadienyl-(5-methylfuran-2-yl) |
| 54 | Zr | dimethylcyclopentadienyl-(3-trifluoromethylphenyl) | dimethylcyclopentadienyl-(3-trifluoromethylphenyl) |
| 55 | Zr | dimethylcyclopentadienyl-(4-trifluoromethylphenyl) | dimethylcyclopentadienyl-(4-trifluoromethylphenyl) |
| 56 | Zr | methylcyclopentadienyl-(3-trifluoromethylphenyl) | methylcyclopentadienyl-(3-trifluoromethylphenyl) |
| 57 | Zr | methylcyclopentadienyl-(4-trifluoromethylphenyl) | methylcyclopentadienyl-(4-trifluoromethylphenyl) |
| 58 | Zr | dimethylcyclopentadienyl-(3-fluorophenyl) | dimethylcyclopentadienyl-(3-fluorophenyl) |

TABLE 1-continued

Metallocene Polymerization Catalysts

| Run # | M | L₁ | L₂ |
|---|---|---|---|
| 59 | Zr | | |
| 60 | Zr | | |
| 61 | Zr | | |
| 62 | Zr | | |

(R-Alk-Cp)(Ar-Cp)

| Run # | M | L₁ | L₂ |
|---|---|---|---|
| 63 | Zr | | |
| 64 | Zr | | |
| 65 | Zr | | |
| 66 | Zr | | |

(Ind)(Ar-Cp)

| Run # | M | L₁ | L₂ |
|---|---|---|---|
| 67 | Zr | | |
| 68 | Zr | | |

TABLE 1-continued

Metallocene Polymerization Catalysts

| Run # | M | L₁ | L₂ |
|---|---|---|---|
| 69 | Zr | indenyl anion | tetraphenylcyclopentadienyl anion |
| 70 | Zr | indenyl anion | 5'-methyl-5-phenyl-2,2'-bithiophene-furan anion |

The compounds provided by the present disclosure are shown above in the summary section and in the claims below. In some embodiments, the compounds can be made using the methods outlined in the Examples section. In some embodiments, the compounds of the present disclosure are synthesized using a method such as that described in Scheme 1. In some embodiments, the unsubstituted or substituted aryl halide are reacted with n-butyl lithium (BuLi) in a nonpolar solvent such as tetrahydrofuran (THF) using a 2 to 1 ratio of BuLi to halide. In some embodiments, the resultant product is then reacted with an equivalent of the desired cyclopentadiene. In some embodiments, the reaction is then worked up using a proton source such as p-toluenesulfonic acid and then may be extracted to yield the desired cyclopentadiene ligand derivative. In some embodiments, the resultant cylcopentadiene ligand is reacted with an equivalent of BuLi in an ether solvent. In some embodiments, after the reaction with BuLi, a half equivalent of ZrCl₄(THF)₂ is added to the reaction mixture. In some embodiments, the complex is precipitated out of solution and is purified through extraction.

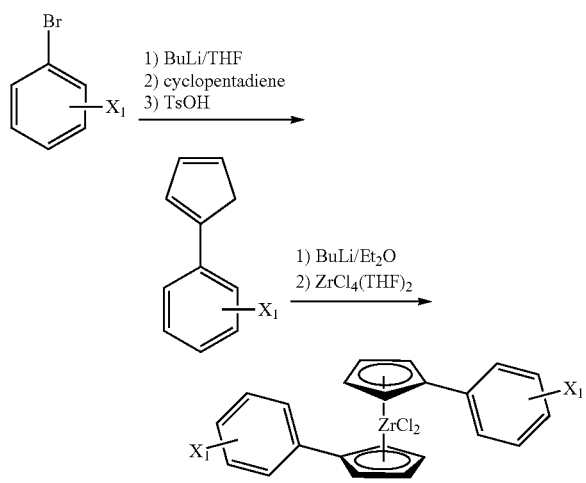

Scheme 1: Generalized Synthetic Scheme for the Preparation of Metallocenes Catalyst Compositions.

These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

In some aspects, the organometallic complexes provided herein are used to generate a catalytically active species which reacts with an alkene monomer to catalyze the production of a polymer. In some embodiments, the it electrons of the alkene form a bond to the metal center which activates the alkene for the next step in the reaction. In some embodiments, the alkene may also undergo oxidative addition to the metal center during the polymerization mechanism. Such catalytic mechanisms are be well known in the art and are taught by *Handbook of Polymer Synthesis Part A* by Kricheldorf, et al., *Principles of Polymerization* by Odian, and *Advanced Inorganic Chemistry*, 5th Edition by Cotton and Wilkinson, for example. In some embodiments, for example, the organometallic catalyst in alkene polymerization is a metallocene which contains a metal of Group 4.

While a complex may use a particular metal in the examples, complexes using other metals within the same group on the periodic table so long as those elements are stable are also contemplated. For example, a metallocene with a zirconium metal core may also in other catalysts contain a hafnium or a titanium metal core. In some embodiments, the labile nature of the ligands around the metallocene affects the reactivity of the catalyst or competes with the alkene's ability to bind to the metal center.

In some embodiments, compounds of the disclosure have the advantage that they may be more catalytically active than, offer more precise control of the resulting polymer, may require a smaller amount of an activating agent, such as aluminoxane, in order to become catalytically active, and/or have other useful physical, or chemical properties over, compounds known in the prior art, whether for use in the processes stated herein or otherwise. In some embodiments, the size of the polymer is controlled by adjusting the ratio of MAO to the metal catalysts. In some embodiments, the higher ratios of MAO to metal lead to less active catalysts and decreased molecular weight of the resultant polymer.

Compounds employed in methods of the disclosure may contain one or more asymmetrically-substituted carbon or nitrogen atoms, and may be isolated in optically active or racemic form. Thus, all chiral, diastereomeric, racemic form, epimeric form, and all geometric isomeric forms of a structure are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present disclosure can have the S or the R configuration, as defined by the IUPAC 1974 Recommendations. For example, mixtures of stereoisomers may be separated using the techniques taught in the Examples section below, as well as modifications thereof.

Atoms making up the compounds of the present disclosure are intended to include all isotopic forms of such atoms. Compounds of the present disclosure include those with one or more atoms that have been isotopically modified or enriched. Isotopes, as used herein, include those atoms having the same atomic number but different mass numbers. By way of general example and without limitation, isotopes of hydrogen include deuterium and tritium, and isotopes of carbon include $^{13}C$ and $^{14}C$. Similarly, it is contemplated that one or more carbon atom(s) of a compound of the present disclosure may be replaced by a silicon atom(s). Furthermore, it is contemplated that one or more oxygen atom(s) of a compound of the present disclosure may be replaced by a sulfur or selenium atom(s).

Bimodal Polyethylene Product Production in a Single Loop Reactor

In some aspects, the present disclosure provides method of making two or more polymers using a single catalyst activated using two or more different methods or activating agents. In some embodiments, the different activated catalyst generates a range of polymers with different molecular weight leading to production which comprises a wide molecular weight distribution. In some embodiments, the catalyst used in the production of the polymers is a metallocene described in this disclosure or known in the literature. In some embodiments, any metallocene which leads to polyethylene production is used. In some embodiments, the catalyst is activated before being introduced into the reaction mixture or slurry. While in other cases, the catalyst is immobilized on a solid support with a large surface area which allows for different areas to be activated using different activating agents. In some embodiments, the solid support has a surface area of greater than 100 m$^2$/g and more preferably 500 m$^2$/g. In some embodiments, the catalyst is activated with aluminoxane such as methylaluminoxane (MAO) and used to generate high molecular weight polymers within the molecular weight distribution. In some embodiments, the aluminoxane is present at a concentration of about 0.001 to about 0.01 M as taught by U.S. Pat. No. 4,752,597, which is incorporated herein by reference. Additionally, in some embodiments, increasing the ratio of aluminoxane to the metal catalyst leads to lower molecular weight polymers within molecular weight distribution produced by the catalytic system. Finally, in some embodiments, borate activators can be used to generate the lowest molecular weight polymers within the polymer molecular weight distribution. In some embodiments, the use of this dual activated catalyst is used in a variety of different polymerization methods including slurry and gas phase polymerization.

Silyl Functionalized Metallocene Derivatives as Polymerization Catalyst

In some aspects, the present disclosure provides silyl functionalized metallocenes which can be used as a polymerization catalyst for the production of higher molecular weight unbranched polymers. In some embodiments, the silyl functionalized metallocenes contain substitutions, such as alkyl groups, or silyl functionalized alkyl groups, on the aryl rings which modify the catalytic effects of the complex. Additionally, in some embodiments, the same silyl functionalized metallocene may react to produce polymers of distinct molecular weights when used with different amounts of an activators such borates or aluminoxanes. In some embodiments, the aluminoxane is methylaluminoxane. In some embodiments, the silyl functionalized metallocene may react the same or differently when exposed to $H_2$ gas than without $H_2$ gas.

Alkene Polymerization Methods

Such metallocene complexes as described in the present disclosure have, in general, been shown that they may be useful in a wide range of polyolefin polymerization process and in a wide range of polymerization methods such as those taught in U.S. Pat. Nos. 4,752,597, 6,756,455, and 7,723,450, all of which are incorporated herein by reference. Other general polymerization methodologies are well known in literature including *Handbook of Polymer Synthesis Part A* by Kricheldorf, et al., *Principles of Polymerization* by Odian, and *Advanced Inorganic Chemistry*, 5$^{th}$ Edition by Cotton and Wilkinson, for example, all of which are incorporated herein by reference. In some embodiments and for the polymerization methods described, the catalyst is present in an amount of roughly 0.00005-0.01% and more preferably approximately 0.005-0.01% by weight of the transition metal as taught by U.S. Pat. No. 4,752,597, which is incorporated herein by reference. In some embodiments of any polymerization method, the temperatures are from about −60° C. to about 300° C., as taught by U.S. Pat. No. 7,723,450. In some embodiments and in solution phase polymerization, the reaction temperature is greater than about 150° C., preferably with in the range from about 200° C. to about 300° C. as taught by U.S. Pat. No. 6,756,455, which is incorporated herein by reference. In some embodiments of a slurry polymerization method, the reaction is carried out at lower temperatures from about 40° C. to about 110° C. as described by U.S. Pat. No. 4,752,597, which is incorporated herein by reference. In some embodiments of any of these polymerization methods, the reaction pressure reaches from about 0.5 bar to about 3000 bar, as taught by U.S. Pat. No. 7,723,450, which is incorporate herein by reference. Additionally, in some embodiments, the reaction time runs from about 30 minutes to about 5 hours with 30 minutes to 3 hours being the preferred length as taught by U.S. Pat. No. 7,723,450, which is incorporate herein by reference. In some embodiments of a slurry polymerization method, the diluent used is an aliphatic or aromatic hydrocarbon solvent or a halogenated version of these solvents. In some embodiments, the inventive catalyst is also used in a gas phase process between the temperatures of 40 and 120° C. The pressures are up to 600 psi. In some embodiments, one or more of the catalysts described in the present disclosure is used in combination with another catalyst to form a hybrid alkene polymerization catalyst system. Additionally, in some embodiments, the methods taught by the present disclosure have been optimized to lead to greater polymer production through a higher activity or to achieve specific characteristics of the desired polymers such a plurality of molecular weights or a specific molecular weight. In some embodiments, the polymerization method taught herein applies to a wide range of terminal alkenes or aralkenes including but not limited to ethylene, propylene, or styrene. In some embodiments, the method is optimized for use with ethylene as the monomer feedstock. In some embodiments, these alkene polymerization methods are used in either a batch or continuous loop reactor. In some embodiments, the reaction additionally contains one or more co-monomers which contain a 1-alkene or 1-aralkene including but not limited to 1-butene, 1-pentene, 1-hexene, 1-octene, or 1-decene, with the preferred embodiment being 1-butene or 1-hexene. In some embodiments, the catalyst and/or the activator are immobilized on a solid support. In some embodiments, such supports include inorganic oxides which are insoluble in the reaction conditions including but not limited to silica, alumina, magnesium oxide, and titanium oxide. In some embodiments, the catalyst which has been exposed to the different activators is attached to the same or different solid support. Furthermore, in some embodiments, the catalysts which have been exposed to different activating agents are added at the same time or different times.

Process Scale-Up

The above methods can be further modified and optimized for preparative, pilot- or large-scale production, either batch or continuous, using the principles and techniques of process chemistry as applied by a person skilled in the art. Such principles and techniques are taught, for example, in *Practical Process Research & Development* (2012), which is incorporated by reference herein.

DEFINITIONS

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; and "amino" means —NH$_2$. When used in the context of a chemical group: "carboxylate" means a molecule which contains the group, —C(=O)O$^-$ (also written as C(O)O$^-$ or —CO$_2^-$) and the overall charge of the molecule is negative or "halide" means a halogen atom formulated as an anion bearing a single negative charge. Any undefined valency on an atom of a structure shown in this application implicitly represents a hydrogen atom bonded to that atom.

In the context of chemical formulas, the symbol "—" means a single bond, "=" means a double bond, and "≡" means triple bond. The symbol "----" represents an optional bond, which if present is either single or double. The symbol "===" represents a single bond or a double bond. Thus, for example, the formula

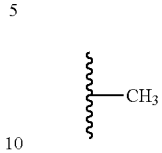

includes

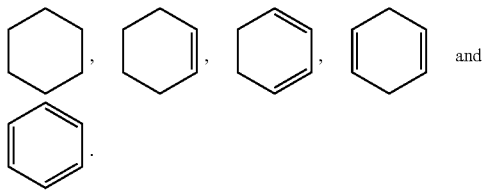

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol " $\sim$ ", when drawn perpendicularly across a bond (e.g.,

—CH$_3$ for methyl) indicates a point of attachment of the group. It is noted that the point of attachment is typically only identified in this manner for larger groups in order to assist the reader in unambiguously identifying a point of attachment. The symbol "◄" means a single bond where the group attached to the thick end of the wedge is "out of the page." The symbol "⫿⫿⫿" means a single bond where the group attached to the thick end of the wedge is "into the page". The symbol " $\sim$ " means a single bond where the geometry around a double bond (e.g., either E or Z) is undefined. Both options, as well as combinations thereof are therefore intended. The bond orders described above are not limiting when one of the atoms connected by the bond is a metal atom (M). In such cases, it is understood that the actual bonding may comprise significant multiple bonding and/or ionic character. Therefore, unless indicated otherwise, the formulas M-C, M=C, M----C, and M ≡ C, each refers to a bond of any type and order between a metal atom and a carbon atom.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms. (Cn-n') defines both the minimum (n) and maximum number (n') of carbon atoms in the group. Similarly, "alkyl$_{(C2-10)}$" designates those alkyl groups having from 2 to 10 carbon atoms.

The term "saturated" as used herein means the compound or group so modified has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkanes/alkenyl).

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl, with the carbon atom that forms the point of attachment also being a member of one or more non-aromatic ring structures wherein the cycloalkyl group consists of no atoms other than carbon and hydrogen. As used herein, the term does not preclude the presence of one or more alkyl groups (carbon number limitation permitting) attached to the ring or ring system. The groups —CH₃ (Me), —CH₂CH₃ (Et), —CH₂CH₂CH₃ (n-Pr or propyl), —CH(CH₃)₂ (i-Pr, ᶦPr or isopropyl), —CH(CH₂)₂ (cyclopropyl), —CH₂CH₂CH₂CH₃ (n-Bu), —CH(CH₃)CH₂CH₃ (sec-butyl), —CH₂CH(CH₃)₂ (isobutyl), —C(CH₃)₃ (tert-butyl, t-butyl, t-Bu or ᵗBu), —CH₂C(CH₃)₃ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH₂— (methylene), —CH₂CH₂—, —CH₂C(CH₃)₂CH₂—, —CH₂CH₂CH₂—, and

are non-limiting examples of alkanediyl groups. It is noted that while the alkenediyl group is aliphatic, once connected at both ends, this group is not precluded from forming an aromatic structure. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH₂, =CH(CH₂CH₃), and =C(CH₃)₂. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, —SiCl₂CH₃, or —S(O)₂NH₂. The following groups are non-limiting examples of substituted alkyl groups: —CH₂OH, —CH₂Cl, —CF₃, —CH₂CN, —CH₂C(O)OH, —CH₂C(O)OCH₃, —CH₂C(O)NH₂, —CH₂C(O)CH₃, —CH₂OCH₃, —CH₂OC(O)CH₃, —CH₂NH₂, —CH₂N(CH₃)₂, and —CH₂CH₂Cl. The term "haloalkyl" is a subset of substituted alkyl, in which one or more hydrogen atoms has been substituted with a halo group and no other atoms aside from carbon, hydrogen and halogen are present. The group, —CH₂Cl is a non-limiting example of a haloalkyl. The term "fluoroalkyl" is a subset of substituted alkyl, in which one or more hydrogen has been substituted with a fluoro group and no other atoms aside from carbon, hydrogen and fluorine are present. The groups, —CH₂F, —CF₃, and —CH₂CF₃ are non-limiting examples of fluoroalkyl groups.

The term "alkenyl" when used without the "substituted" modifier refers to an monovalent unsaturated aliphatic group with a carbon atom as the point of attachment, a linear or branched, cyclo, cyclic or acyclic structure, at least one non-aromatic carbon-carbon double bond, no carbon-carbon triple bonds, and no atoms other than carbon and hydrogen. Non-limiting examples of alkenyl groups include: —CH=CH₂ (vinyl), —CH=CHCH₃, —CH=CHCH₂CH₃, —CH₂CH=CH₂ (allyl), —CH₂CH=CHCH₃, and —CH=CHCH=CH₂. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH₃)CH₂—, —CH=CHCH₂—, and

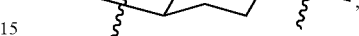

are non-limiting examples of alkenediyl groups. The terms "alkene" or "olefin" are synonymous and refer to a compound having the formula H—R, wherein R is alkenyl as this term is defined above. A "terminal alkene" refers to an alkene having just one carbon-carbon double bond, wherein that bond forms a vinyl group at one end of the molecule. When any of these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, —SiCl₂CH₃, or —S(O)₂NH₂. The groups, —CH=CHF, —CH=CHCl and —CH=CHBr, are non-limiting examples of substituted alkenyl groups.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH₃, and —CH₂C≡CCH₃, are non-limiting examples of alkynyl groups. An "alkyne" refers to the compound H—R, wherein R is alkynyl. When any of these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, —SiCl₂CH₃, or —S(O)₂NH₂.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C₆H₄CH₂CH₃ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include

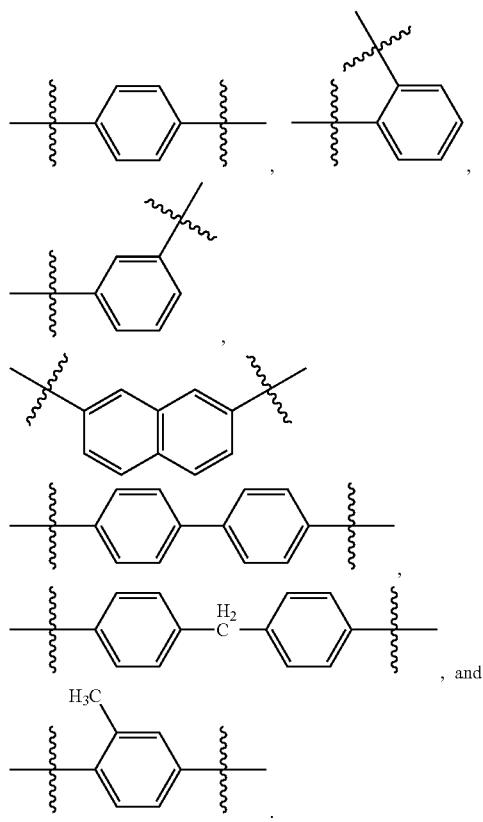

, and

An "arene" refers to the compound H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —SiCl$_2$CH$_3$, or —S(O)$_2$NH$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —SiCl$_2$CH$_3$, or —S(O)$_2$NH$_2$. Non-limiting examples of substituted aralkyls are: (3-chlorophenyl)-methyl, and 2-chloro-2-phenyl-eth-1-yl.

The term "aralkenyl" when used without the "substituted" modifier refers to the monovalent group -alkenediyl-aryl, in which the terms alkenediyl and aryl are each used in a manner consistent with the definitions provided above. Non-limiting examples of aralkenyls are: 2-phenylethenyl and 3,3-diphenyl-prop-2-enyl. The term "aralkene" refer to a compound having the formula H—R, wherein R is aralkenyl as this term is defined above. A "terminal aralkene" refers to an aralkene having just one non-aromatic carbon-carbon double bond, wherein that bond forms a vinyl group at one end of the molecule. When the term is used with the "substituted" modifier one or more hydrogen atom from the alkanediyl and/or the aryl has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, —SiCl$_2$CH$_3$, or —S(O)$_2$NH$_2$. Non-limiting examples of substituted aralkenyls are: (3-nitrophenyl)-ethenyl, and 4-cyano-4-phenyl-but-1-enyl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl, aryl, and/or aralkyl groups (carbon number limitation permitting) attached to the aromatic ring or aromatic ring system. Non-limiting examples of heteroarenediyl groups include:

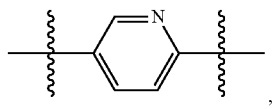

,

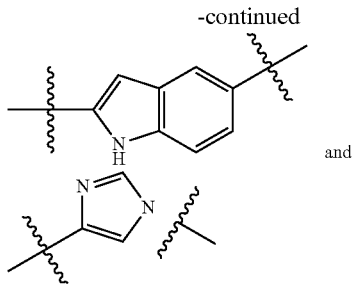

and

A "heteroarene" refers to the compound H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —SiCl$_2$CH$_3$, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. The term "heterocycloalkanediyl" when used without the "substituted" modifier refers to an divalent cyclic group, with two carbon atoms, two nitrogen atoms, or one carbon atom and one nitrogen atom as the two points of attachment, said atoms forming part of one or more ring structure(s) wherein at least one of the ring atoms is nitrogen, oxygen or sulfur, and wherein the divalent group consists of no atoms other than carbon, hydrogen, nitrogen, oxygen and sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkanediyl groups include:

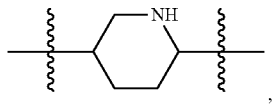

,

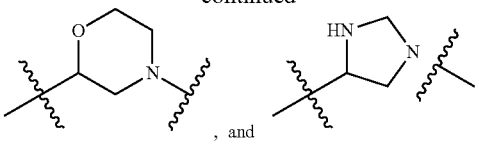

, and

.

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —S(O)$_2$NH$_2$, —SiCl$_2$CH$_3$, or —C(O)OC(CH$_3$)$_3$ (tert-butyloxycarbonyl, BOC).

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, C(O)CH(CH$_2$)$_2$, C(O)C$_6$H$_5$, —C(O)C$_6$H$_4$CH$_3$, —C(O)CH$_2$C$_6$H$_5$, —C(O)(imidazolyl) are non-limiting examples of acyl groups. When either of these terms are used with the "substituted" modifier one or more hydrogen atom (including a hydrogen atom directly attached the carbonyl, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —SiCl$_2$CH$_3$, or —S(O)$_2$NH$_2$. The groups, —C(O)CH$_2$CF$_3$, —CO$_2$H (carboxyl), —CO$_2$CH$_3$ (methylcarboxyl), CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$ (methoxy), —OCH$_2$CH$_3$ (ethoxy), —OCH$_2$CH$_2$CH$_3$, —OCH(CH$_3$)$_2$ (isopropoxy), —O(CH$_3$)$_3$ (tert-butoxy), —OCH(CH$_2$)$_2$, —O-cyclopentyl, and —O-cyclohexyl. The terms "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is alkenyl, alkynyl, aryl, aralkyl, heteroaryl, heterocycloalkyl, and acyl, respectively. The term "alkoxydiyl" refers to the divalent group —O-alkanediyl-, —O-alkanediyl-O—, or -alkanediyl-O-alkanediyl-. The term "alkylthio" and "acylthio" when used without the "substituted" modifier refers to the group —SR, in which R is an alkyl and acyl, respectively. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —SiCl$_2$CH$_3$, or —S(O)$_2$NH$_2$. The term "alcohol" corresponds to an alkane, as defined above, wherein at least one of the hydrogen atoms has been replaced with a hydroxy group. Similarly, the term "ether" corresponds to an alkane, as defined above, wherein at least one of the hydrogen atoms has been replaced with an alkoxy group. Additionally, the addition of the suffix "late" such as in the term "alkoxylate" or "heteroaryloxylate" refers to the group $^-$OR where the oxygen atom has a negative charge and R is defined as appropriate for the prefix using the definitions above.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", "heterocycloalkylamino" and "alkylsulfonylamino" when used without the "substituted" modifier, refers to groups, defined as —NHR, in which R is alkoxy, alkenyl, alkynyl, aryl, aralkyl, heteroaryl, heterocycloalkyl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —SiCl$_2$CH$_3$, or —S(O)$_2$NH$_2$. The groups —NHC(O)OCH$_3$ and —NHC(O)NHCH$_3$ are non-limiting examples of substituted amido groups.

The term "metallocene" is used to indicate a metal complex with at least two ligands are aromatic rings where the metal interacts with the ligand through the aromatic molecular orbitals. The aromatic rings may be an electron rich aromatic system such as but not limited to the negatively charged cyclopentadienyl or an indole, wherein cyclopentadienyl is the preferred ligand. The metal center of the complex may be a transition metal of groups 3, 4, 5, 6, 7, 8, 9, or 10. The transition metals of group 3 include scandium (Sc), yttrium (Y), lanthanum (La), actinium (Ac), lutetium (Lu) and lawrencium (Lr). The metals of group 4 include titanium, zirconium, hafnium, and rutherfordium. The transition metals of group 5 include vanadium (V), niobium (Nb), tantalum (Ta) and dubnium (Db). The transition metals of group 6 include chromium (Cr), molybdenum (Mo), tungsten (W), and seaborgium (Sg). The transition metals of group 7 include manganese (Mn), technetium (Tc), rhenium (Re), and bohrium (Bh). The transition metals of group 8 include iron (Fe), ruthenium (Ru), osmium (Os) and hassium (Hs). The transition metals of group 9 include cobalt (Co), rhodium (Rh), iridium (Ir), and meitnerium (Mt). The transition metals of group 10 include nickel (Ni), palladium (Pd), platinum (Pt), and darmstadtium (Ds). The complex may further comprise one or more ligands in addition to the aromatic rings such as but not limited to halides or carboxylates.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "hybrid alkene polymerization catalyst system" is defined as a catalyst system comprising one or more late transition metal catalyst, one or more metallocene catalysts, and one or more activating complexes. Additionally, the system may also comprise a solid support for the immobilization of one or more of the late transition metal catalysts, metallocene catalysts, or activating complexes. The late transition metal catalyst may be a catalyst described in U.S. Pat. No. 8,435,911, which is incorporated herein by reference, or other similar polyolefin polymerization catalyst containing a late transition metal. Additionally, the metallocene portion of the catalyst system can be a metallocene described in the present disclosure or any suitable metallocene which has been shown to act as a polyolefin polymerization catalyst. The activating compound could be an aluminoxane or boron containing compound such as borane or boroxines. In particular the aluminoxane could be methyl aluminoxane and contains a cyclic or open chain form such as those described in the present disclosure or in U.S. Pat. No. 8,435,911, which is incorporated herein by reference. The boron containing activator include the activator such as those described in U.S. Pat. No. 8,435,911, PCT Publication No. WO 05/103096, or PCT Publication No. WO 97/36937, which are all incorporated herein by reference. Additional activator compounds or complexes include those described in PCT Publication No. WO 00/31090 or PCT Publication No. WO 99/06414, both of which are incorporated herein by reference. Furthermore, the solid support could be silica gel, aluminum oxide, mesoporous materials, aluminosilicates, hydrotalcites, organic polymers or polymers containing polar functionalities such as copolymers of ethane and acrylic esters, acrolein, or vinyl acetates. Additionally, the system may comprise an additional organometallic or metallic compound such as those described in WO 05/103096, which is incorporated herein by reference.

An "isomer" of a first compound is a separate compound in which each molecule contains the same constituent atoms as the first compound, but where the configuration of those atoms in three dimensions differs.

A "method" is series of one or more steps undertaking lead to a final product, result or outcome. As used herein, the word "method" is used interchangeably with the word "process".

The above definitions supersede any conflicting definition in any reference that is incorporated by reference herein. The fact that certain terms are defined, however, should not be considered as indicative that any term that is undefined is indefinite. Rather, all terms used herein are believed to describe the embodiments as described herein in terms such that one of ordinary skill can appreciate the scope and practice the embodiments of the present disclosure.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Synthesis of Metallocene Complexes

Complex 11:

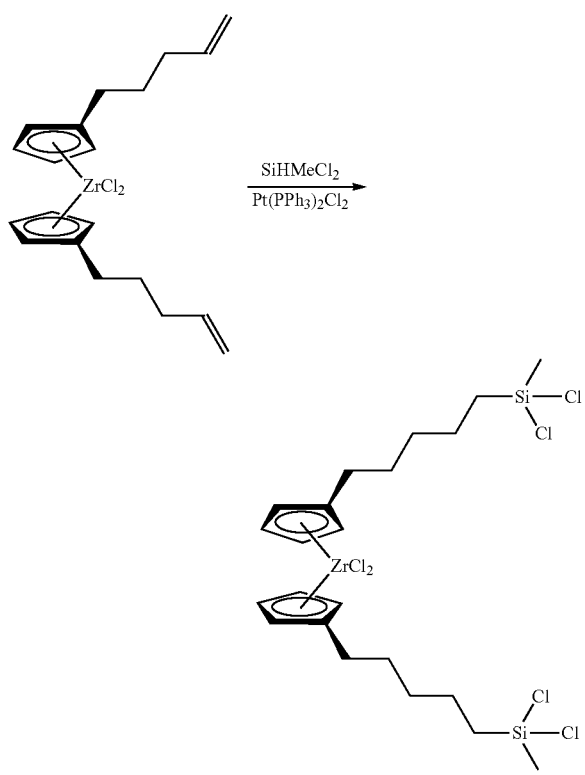

Pt(PPh$_3$)$_2$Cl$_2$ (57 mg, 72 mmol) was added to solution of complex 338 (1.03 g, 2.4 mmol) and SiHMeCl$_2$ (1.15 g, 10 mmol) in toluene (25 mL). The mixture was heated with stirring at 60° C. for 6 h, and 16 h at room temperature. The solvent was removed under reduced pressure, the residue was recrystallized from pentane yielding 0.59 g (37%) of the product.

$^1$H NMR (CDCl$_3$): δ 6.30 (t, 4H); 6.20 (t, 4H); 2.64 (t, 4H); 1.61-1.40 (m, 12H); 1.12 (m, 4H); 0.76 (s, 6H).
$^{13}$C NMR (CDCl$_3$): δ 134.84; 116.74; 112.06; 31.94; 30.01; 29.89; 22.18; 21.47; 5.18.

Complex 12:

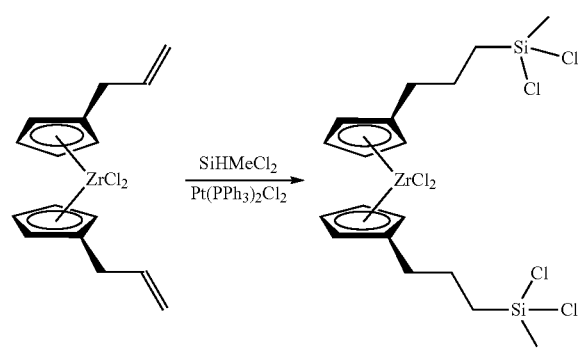

Pt(PPh$_3$)$_2$Cl$_2$ (60 mg, 75 mmol) was added to solution of complex 332 (0.56 g, 1.5 mmol) and SiHMeCl$_2$ (0.6 g, 6 mmol) in toluene (15 mL). The mixture was heated with stirring at 60° C. for 6 h, and 16 h at room temperature. The solvent was removed under reduced pressure, the residue was recrystallized from pentane yielding 0.56 g (64%) of the product.

$^1$H NMR (CDCl$_3$): δ 6.32 (m, 4H); 6.23 (m, 4H); 2.73 (t, 4H); 1.77 (m, 4H); 1.14 (m, 4H); 0.77 (s, 6H).
$^{13}$C NMR (CDCl$_3$): δ 133.75; 117.02; 112.10; 32.61; 23.73; 21.28; 5.18.

Complex 18:

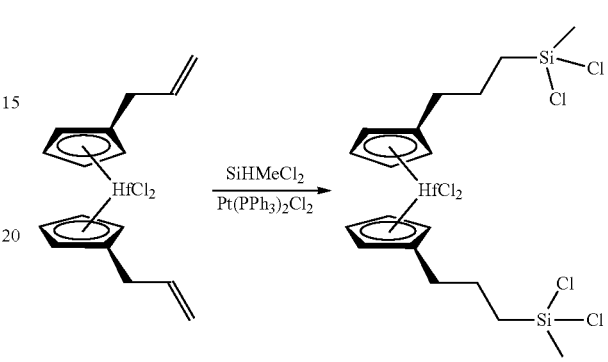

Pt(PPh$_3$)$_2$Cl$_2$ (35 mg, 44 mmol) was added to solution of complex 335 (1.01 g, 2.2 mmol) and SiHMeCl$_2$ (0.76 g, 6.6 mmol) in toluene (20 mL). The mixture was heated with stirring at 60° C. for 6 h, and 16 h at room temperature. The solvent was removed under reduced pressure, and the residue was recrystallized from pentane yielding 0.79 g (52%) of the product.

$^1$H NMR (CDCl$_3$): δ 6.22 (m, 4H); 6.12 (m, 4H); 2.75 (t, 4H); 1.77 (m, 4H); 1.14 (m, 4H); 0.77 (s, 6H).
$^{13}$C NMR (CDCl$_3$): δ 131.62; 115.58; 110.80; 32.51; 23.93; 21.30; 5.17.

Complex 20:

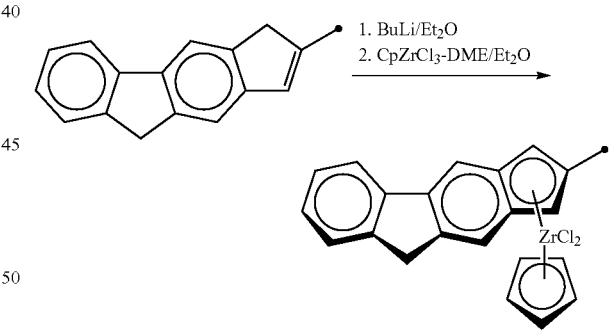

(1,2,3,3a,10a-η$^5$-2-methyl-3,9-dihydrocyclopenta[b]fluorenyl)(η$^5$-cyclopentadienyl)dichlorozirconium
(IV)

n-BuLi (1.6M solution in hexane, 9.4 ml, 15 mmol) was added to cooled (−40° C.) solution of 2-methyl-3,9-dihydrocyclopenta[b]fluorene in Et$_2$O (40 ml). The mixture was allowed to warm to room temperature, stirred for 3 h, cooled to −40° C., and CpZrCl$_3$(DME) (5.29 g, 15 mmol) was added. Resulting mixture was allowed to warm to room temperature, stirred for 16 h, and filtered. Resulting precipitate was recrystallized from CH$_2$Cl$_2$-pentane (1:1). The yield 2.46 g (37%), yellow crystalline powder.

$^1$H NMR (CDCl$_3$, 20° C.) δ: 2.38 (s, 3H, —CH$_3$); 4.05 (AB, 2H, $^2$J=22 Hz, —CH$_2$—); 6.04 (s, 5H, C$_5$H$_5$); 6.30 (s, 1H); 6.35 (s, 1H) {—CH═}; 7.35-7.44 (m, 2H); 7.55 (d, $^3$J=7.3 Hz, 1H); 7.74 (s, 1H); 7.88 (d, $^3$J=7.1 Hz); 7.96 (s, 1H) {C$_{Ar}$—H}.

$^{13}$C NMR (CDCl$_3$, 20° C.) δ: 17.5; 36.2; 104.1; 104.4; 114.4; 116.4; 120.5; 120.7; 125.4; 125.9; 127.2; 128.2; 133.9; 140.1; 140.4; 141.6; 143.5.

Complex 21:

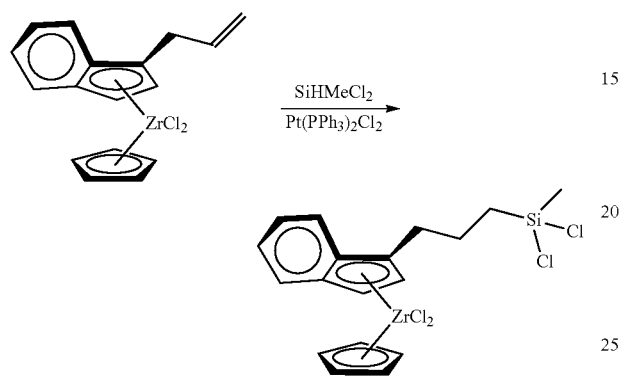

Prepared by procedure used for Complex 24.

$^1$H NMR (CDCl$_3$): δ 7.65 (m, 2H); 7.29 (m, 2H); 6.69 (bs, 1H); 6.48 (bs, 1H); 6.15 (s, 5H); 3.14 (m, 1H); 2.98 (m, 1H); 1.87 (m, 2H); 1.20 (m, 2H); 0.77 (s, 3H).

$^{13}$C NMR (CDCl$_3$): δ 126.40; 126.05; 125.52; 125.49; 124.85; 124.41; 123.88; 121.21; 120.67; 30.43; 21.46; 5.18.

Complex 24:

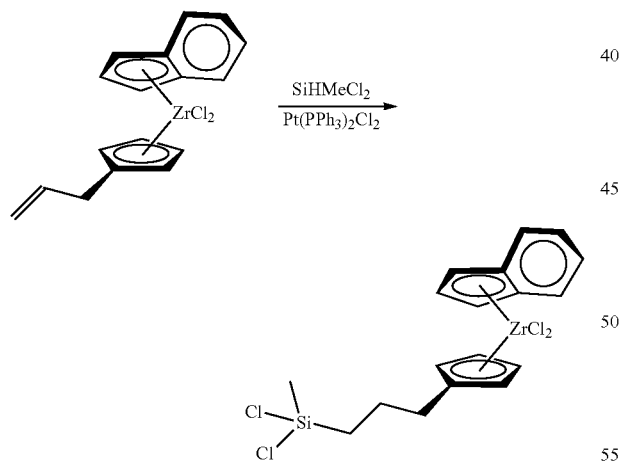

Pt(PPh$_3$)$_2$Cl$_2$ (31 mg, 40 mmol) was added to solution of (Ind)(AllylCp)ZrCl$_2$ (0.79 g, 2 mmol) and SiHMeCl$_2$ (0.46 g, 4 mmol) in toluene (15 mL). The mixture was heated with stirring at 60° C. for 6 h, and 16 h at room temperature. The solvent was removed under reduced pressure, the residue was recrystallized from pentane yielding 0.44 g (44%) of the product.

$^1$H NMR (CDCl$_3$): δ 7.70 (m, 2H); 7.32 (m, 2H); 6.94 (t, 1H); 6.54 (m, 2H); 5.96 (bs, 2H); 5.89 (bs, 2H); 2.62 (t, 2H); 1.69 (m, 2H); 1.09 (m, 2H); 0.76 (s, 3H).

Complex 25:

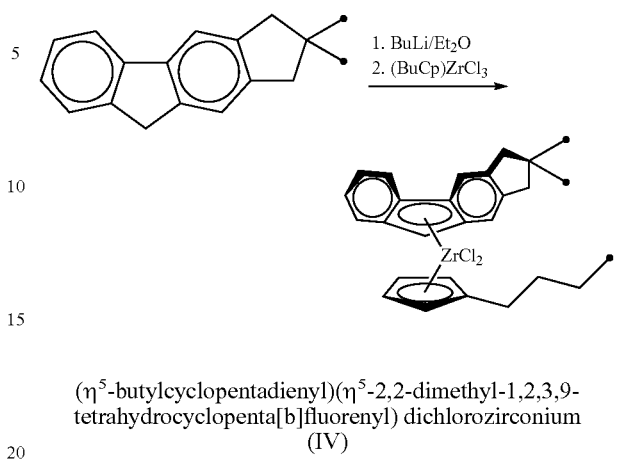

(η$^5$-butylcyclopentadienyl)(η$^5$-2,2-dimethyl-1,2,3,9-tetrahydrocyclopenta[b]fluorenyl) dichlorozirconium (IV)

n-BuLi (2.5M solution in hexane, 2.1 ml, 5.2 mmol) was added to cooled (−40° C.) solution of 2,2-dimethyl-1,2,3,9-tetrahydrocyclopenta[b]fluorene (1.17 g, 5 mmol) in Et$_2$O (40 ml). The mixture was allowed to warm to room temperature, stirred for 3 h, cooled to −40° C., and (BuCp)ZrCl$_3$× DME (2.13 g, 5.2 mmol) was added. The mixture was allowed to warm to room temperature and stirred for 16 h. TMEDA (1.5 ml, ~10 mmol) was added, and the mixture was filtered. Yellow precipitate was washed by ether (20 ml) and pentane (30 ml). The product was recrystallized (hexane-toluene, 1:3) and dried in vacuo. The yield 0.86 g (33%).

$^1$H NMR (CDCl$_3$, 20° C.) δ: 0.87 (t, 3J=7.3 Hz, 3H); 1.16 (s, 3H); 1.21 (s, 2H); 1.27 (m, 2H); 1.42 (m, 2H) 2.80 (br., 2H); 2.84 (d, 1H, $^2$J=15.7 Hz); 2.96 (d, 1H, $^2$J=15.7 Hz); 5.84-5.96 (m, 4H, Cp ring); 6.43 (s, 1H); 7.26-8.07 (group of m, 5H, C$_{Ar}$—H).

Complex 26:

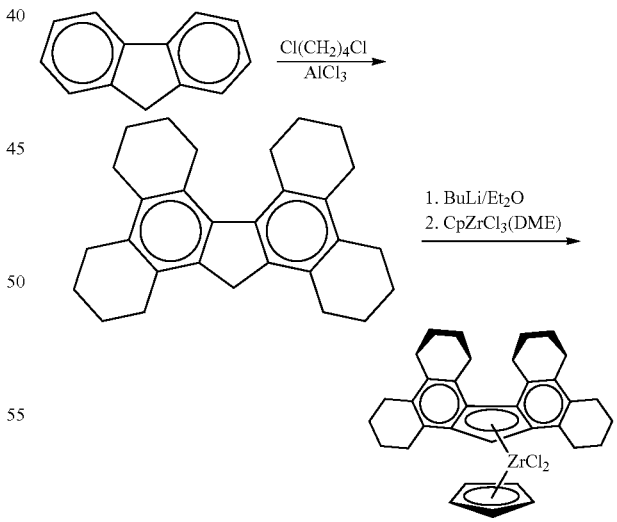

9,9'-methylene-10,10'-bi(1,2,3,4,5,6,7,8-octahydrophenanthrenyl) or hexadecahydrotetrabenzo[a,c,d,f]fluorene Fluorene (12.5 g, 75.2 mmol) was dissolved in 1,4-dichlorobutane (76.4 g, 602 mmol). Clear solution was cooled with stirring to −20° C., and AlCl₃ (5.0 g, 37.6 mmol) was added. Reaction mixture was allowed to warm to room temperature, stirred for 16 h at 20° C. and 72 h at 60-80° C., poured into ice/HCl. Organic layer was separated, aqueous layer was extracted by CHCl₃ (350 ml). Combined organic phase was washed by water, Na₂CO₃, dried over Na₂SO₄ and evaporated. Ether (150 ml) was added, after 16 h yellow precipitate was filtered off and dried in vacuo. The yield 3.45 g (12%).

¹H NMR (CDCl₃, 20° C.) δ: 1.70 (br., 4H); 1.92 (br, 12H); 2.70-2.85 (group of br., 12H); 3.09-3.22 (br, 4H); 3.54 (s, 2H).

¹³C NMR (CDCl₃, 20° C.) δ: 22.6; 23.31; 23.34; 23.5; 26.8; 27.0; 27.1; 33.3; 34.6; 129.8; 130.6; 133.6; 133.7; 139.6; 139.9.

Complex 30:

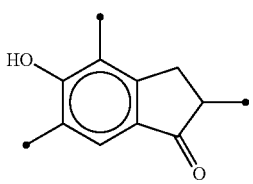

5-Hydroxy-2,4,6-trimethylindan-1-one

Solution of 2,6-dimethylphenol (36.65 g, 0.3 mol) in CH₂Cl₂ (100 ml) was added to well stirred suspension of AlCl₃ (120 g, 0.9 mol) in CH2Cl2 (200 ml). After 20 min, 2-bromoisobutyryl bromide (69 g, 0.3 mol) was added. Reaction mixture was stirred for 3 days, poured into HCl/crashed ice, organic phase was separated, water phase was extracted by CH₂Cl₂ (3×100 ml), combined organic fraction was washed by water, dried over MgSO₄, and evaporated. Ether (70 ml) and hexane (70 ml) were added, resulting crystalline precipitate was filtered off and dried in vacuo. The yield 15.8 g (27.7%).

NMR ¹H (CDCl₃) δ: 7.45 (s, 1H); 6.05 (broad, 1H); 3.25 (dd, 1H); 2.69 (m, 1H); 2.54 (dd, 1H); 2.29 (s, 3H); 2.22 (s, 3H); 1.30 (d, 3H).

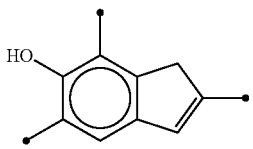

2,5,7-Trimethyl-1H-inden-6-ol

Suspension of 5-hydroxy-2,4,6-trimethylindan-1-one (4.74 g, 24.9 mmol) in THF (30 ml) was added at 0° C. to suspension of LiAlH₄ (0.94 g, 24.9 mmol) in THF (50 ml). The mixture was allowed to warm to room temperature, stirred for 2 h. 5% HCl (20 ml) was added, resulting mixture was extracted by CH₂Cl₂ (4×50 ml), combined organic fraction was washed by water, dried over MgSO₄, passed through silica gel, and evaporated. Residue was washed by cold pentane and dried in vacuo. The yield 3.75 g (86%).

NMR ¹H (CDCl₃) δ: 6.88 (s, 1H); 6.37 (s, 2H); 4.47 (broad s, 1H); 3.16 (s, 2H); 2.26 (s, 3H); 2.23 (s, 3H); 2.12 (s, 3H).

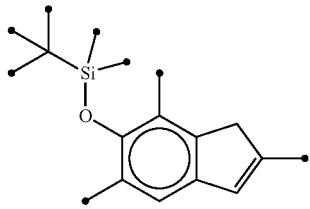

tert-Butyl(dimethyl)[(2,5,7-trimethyl-1H-inden-6-yl)oxy]silane

Mixture of 2,5,7-trimethyl-1H-inden-6-ol (1.8 g, 10.3 mmol), imidazole (1.76 g, 25.8 mmol), and tert-butylchlorodimethylsilane (1.87 g, 12.4 mmol) in CH₃CN (35 ml) was stirred for 16 h at room temperature, poured into 2% HCl (100 ml), extracted by pentane (4×20 ml). Combined organic fraction was washed by water, dried over MgSO4, and evaporated. The yield 2.8 g (94%).

NMR ¹H (CDCl₃) δ: 6.89 (s, 1H); 6.38 (s, 2H); 3.14 (s, 2H); 2.24 (s, 3H); 2.19 (s, 3H); 2.13 (s, 3H), 1.06 (s, 9H); 0.19 (s, 6H).

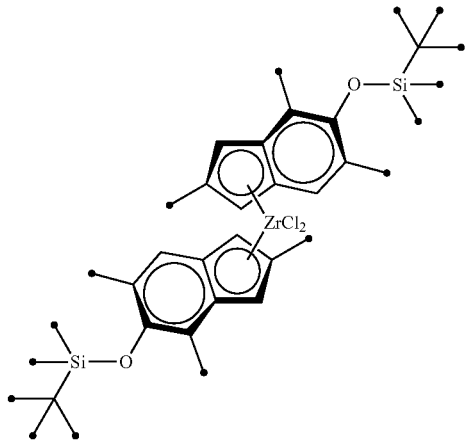

Bis(η⁵-2,5,7-trimethyl-6-tert-butyldimethylsiloxy-1H-indenyl)dichlorozirconium (IV)

BuLi (1.6M in hexane, 2.1 ml, 3.3 mmol) was added at −20° C. to the solution of tert-butyl(dimethyl)[(2,5,7-trimethyl-1H-inden-6-yl)oxy]silane (0.87 g, 3 mmol) in Et₂O (25 ml). Reaction mixture was allowed to warm to room temperature, stirred for 1 h, cooled to −40° C., ZrCl₄ (0.37 g, 1.6 mmol) was added. Reaction mixture was stirred for 2 h at −40° C., allowed to warm to room temperature, stirred for 16 h. The solution was separated by decantation, evaporated, the residue was recrystallized from hexane. The yield 0.48 g (43%), yellow crystalline powder.

NMR ¹H (CDCl₃) for mixture of isomers δ: 7.25 (s, 2H); 6.14 (s, 2H); 5.85 (s, 2H); 2.28 (s, 6H); 2.27 (s, 6H); 2.24 (s, 6H); 1.07 (s, 18H); 0.15 (s, 12H), and 6.98 (s, 2H); 6.21 (s, 2H); 6.05 (s, 2H); 2.34 (s, 6H); 2.24 (s, 6H); 1.93 (s, 6H); 1.07 (s, 18H); 0.27 (s, 6H); 0.21 (s, 6H).

Complex 32:

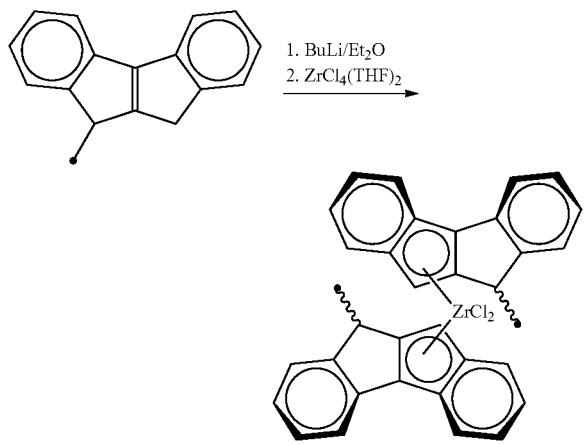

Bis-(5a,6,6a,10a,10b-η$^5$-5-methyl-5,6-dihydroindeno[1,2-a]indenyl)dichlorozirconium (IV)

n-BuLi (2.5M, 6.1 ml, 15.2 mmol) was added at –40° C. to solution of 5-methyl-5,6-dihydroindeno[1,2-a]indene (3.27 g, 15 mmol) in Et$_2$O (50 ml). The mixture was allowed to warm to room temperature, stirred for 3 h, cooled to –20° C., and ZrCl$_4$(THF)$_2$ (2.86 g, 7.6 mmol) was added. After 16 h of stirring, the precipitate was filtered off, washed by Et$_2$O, pentane and recrystallized from toluene. The yield 1.06 g (24%).

$^1$H NMR (CDCl$_3$, 20° C.) δ: 1.18 (d); 1.34 (d) {3H, —CH$_3$}; 3.19 (q); 3.30 (q) {1H}; 6.02 (s); 6.24 (s) {1H}; 6.80-7.96 (groups of m, 16H).

Complex 48:

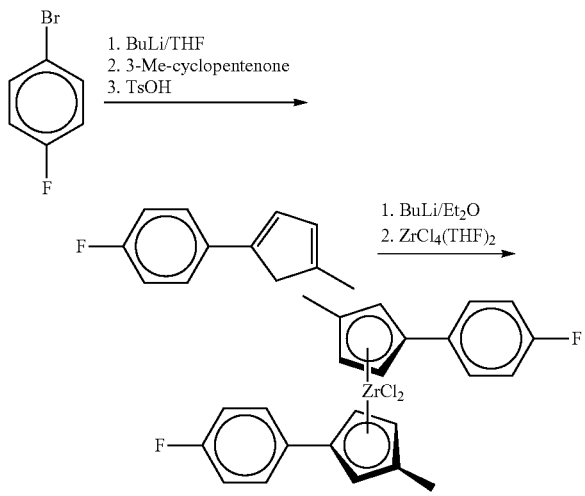

1-Fluoro-4-(4-methyl-1,4-cyclopentadien-1-yl)benzene

The solution of 1-bromo-4-fluorobenzene (26.3 g, 150 mol) in 200 mL of Et$_2$O was cooled to –50° C. and BuLi (94 mL, 1.6 M in hexane, 150 mmol) was added. The mixture was stirred at this temperature for 40 min and warmed to 0° C. Then the solution of 3-methylcyclopenen-2-one (14.4 g, 150 mmol) in 15 mL of ether was added and mixture was stirred overnight. Water (30 mL) was added. The organic layer was separated, washed by brine and concentrated to 100 mL. TsOH (0.5 g) was added and mixture was refluxed for 1 min. After cooling mixture was washed by 5% NaHCO$_3$, brine, dried over MgSO$_4$, solvent was evaporated and residue was recrystallized from methanol. The yield was 10.5 g (40%).

$^1$H NMR (CDCl$_3$): δ 7.48 (m, 2H); 7.05 (m, 2H); 6.70-6.04 (m, 2H); 3.45 (m, 2H); 2.09 (s, 3H).

1-Fluoro-4-(4-methyl-1,4-cyclopentadien-1-yl)benzene (7 g, 40 mmol) was dissolved in mixture of 50 mL of THF and 30 mL of hexane, cooled to –40° C. and treated with BuLi (25 mL, 1.6 M in hexane, 40 mmol). Mixture was stirred at this temperature for 2 h, and warmed to 0° C. The resulting solution was cooled to –70° C. and ZrCl$_4$(THF)$_2$ (7.5 g, 20 mmol) was added. The mixture was stirred overnight at room temperature, filtered, and the filtrate was evaporated. The residue was treated by mixture of hexane (60 mL) and dichloromethane (15 mL). Precipitate was filtered off, washed with pentane and dried. The yield 6.2 g (62%).

$^1$H NMR (CDCl$_3$): δ 7.40 (m, 4H); 7.10 (m, 4H); 6.48 (t, 1H); 6.43 (t, 1H); 6.38 (t, 1H); 6.33 (t, 1H); 5.84 (m, 2H); 2.16 (s, 3H); 2.11 (s, 3H).

Complex 50:

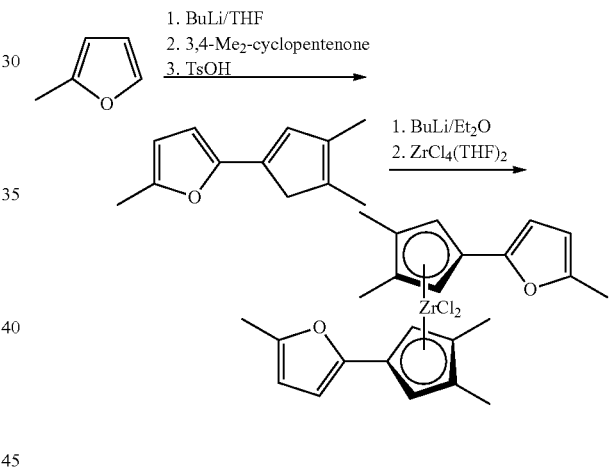

2-(3,4-Dimethyl-1,3-cyclopentadien-1-yl)-5-methylfuran

The solution of 2-methylfurane (9 mL, 100 mmol) in 120 mL THF was cooled to 0° C., and BuLi (50 mL, 1.6 M in hexane, 80 mmol) was added dropwise. After 1.5 h the solution of 3,4-dimethylcyclopenen-2-one (8.8 g, 80 mmol) in 10 mL of ether was added at the same temperature. After 16 h of stirring, water (2 mL) was added, solution was separated from precipitate and precipitate was washed by 20 mL of ether. TsOH (0.5 g) was added to combined solution, the mixture was heated to reflux, cooled, washed by NaHCO$_3$, brine, dried over MgSO$_4$ and evaporated. Residue was distilled in vacuo (B. p. 75-77° C./0.8 torr), yielding the product (8.3 g, 60%).

$^1$H NMR (CDCl$_3$): δ 6.48 (s, 1H); 6.11 (d, 1H); 5.96 (m, 1H); 3.21 (s, 2H); 2.33 (s, 3H); 1.97 (s, 3H); 1.90 (d, 3H).

Solution of 2-(3,4-dimethyl-1,3-cyclopentadien-1-yl)-5-methylfuran (4.2 g, 24 mmol) in Et$_2$O (40 mL) was cooled to 0° C. and BuLi (15 mL, 1.6 M in hexane, 24 mmol) was added dropwise. Mixture was stirred for 2 h at room temperature, cooled again, and ZrCl$_4$(THF)$_2$ (4.5 g, 12 mmol) was added.

The mixture was stirred overnight, filtered, the filtrate was evaporated. The residue crystallizes slowly. Solid product was washed with pentane and dried. The yield was 2.8 g (46%).

$^1$H NMR (CDCl$_3$): δ 6.36 (s, 4H); 6.28 (d, 2H); 6.07 (d, 2H); 2.43 (s, 6H); 1.84 (s, 12H).

Complex 51:

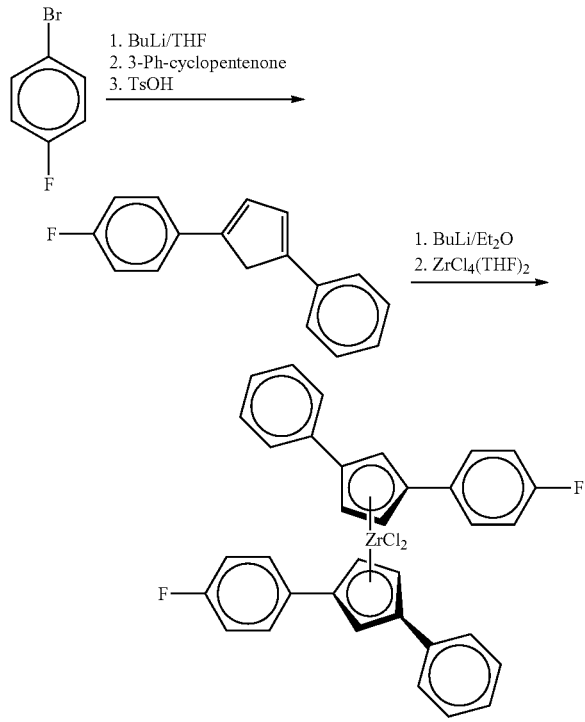

1-Fluoro-4-(4-methyl-1,4-cyclopentadien-1-yl)benzene

The solution of 1-bromo-4-fluorobenzene (8.75 g, 50 mol) in 100 mL of Et$_2$O was cooled to −50° C. and BuLi (32 mL, 1.6 M in hexane, 50 mmol) was added dropwise, the mixture was stirred at this temperature for 40 min and warmed to 0° C. The solution of 3-phenyl-cyclopenene-2-on (7.9 g, 50 mmol) in 40 mL of THF was added and mixture was stirred overnight. Mixture was treated by 30 mL of 10% NH$_4$Cl, and then organic layer was separated and washed by brine. Then TsOH (0.5 g) was added, the mixture was refluxed for 1 min. After cooling the mixture was washed by 5% NaHCO$_3$, brine, dried over MgSO$_4$. Solvent was evaporated, and the residue was recrystallized (ethanol), yielding 6.8 g of the product as a mixture of isomers (58%).

$^1$H NMR (CDCl$_3$): δ 7.61 (m, 4H); 7.40 (m, 2H); 7.26 (m, 2H); 7.09 (m, 2H), 6.65 (m, 1H); 6.60 (m, 1H); 3.60 (d, 2H).

The solution of 1-fluoro-4-(4-methyl-1,4-cyclopentadien-1-yl)benzene (3 g, 12.7 mmol) in Et$_2$O (40 mL) was cooled to 0° C., and BuLi (8 mL, 1.6 M in hexane, 13 mmol) was added dropwise. Mixture was stirred for 2 h at room temperature, cooled again to 0° C., and ZrCl$_4$(THF)$_2$ (2.4 g, 6.3 mmol) was added. After 16 h of stirring, the yellow precipitate was filtered off, dissolved in dichloromethane, and solvent was evaporated. Residue was extracted by toluene-hexane mixture (3:1, 70 mL). Solvent was evaporated, and the residue was dried in vacuo. The yield was 1.7 g (1:1 mixture of isomers).

$^1$H NMR (CDCl$_3$): δ 7.42 (m, 14H); 7.02 (m, 6H); 6.35 (m, 2H); 6.27 (m, 2H).

Complex 52:

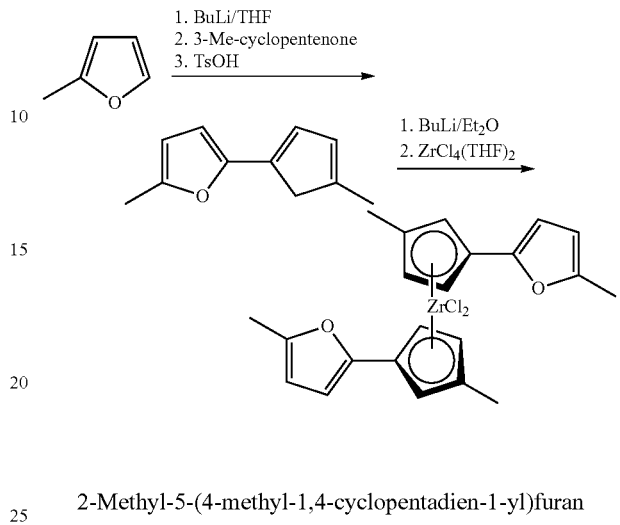

2-Methyl-5-(4-methyl-1,4-cyclopentadien-1-yl)furan

The solution of 2-methylfuran (8.2 g, 100 mmol) in 120 mL of abs. THF was cooled to 0° C. and BuLi (50 mL 2.5N in hexane, 80 mmol) was added dropwise and stirred at this temperature for 1.5 h. The solution of 3-methylcyclopenen-2-one (7.7 g, 80 mmol) in 10 mL of THF was added and mixture was stirred overnight. Mixture was treated by 3 mL of water, organic layer was separated. TsOH (0.5 g) was added, and the mixture was refluxed for 1 min. After cooling the mixture was washed by 5% NaHCO$_3$, brine, dried over MgSO$_4$, solvent was evaporated and residue was distilled in vacuo, yielding 6.5 g of product as mixture of 3 isomers (yield 50%, b.p. 70-71° C./1 torr).

$^1$H NMR (CDCl$_3$): δ 6.57 (s, 1H); 6.22 (d, 1H); 5.99 (m, 1H); 5.91 (m, 1H); 3.28 (s, 2H); 2.35 (s, 3H); 2.04 (s, 3H).

The solution of 2-(3,4-dimethyl-1,3-cyclopentadien-1-yl)-5-methylfuran (3.2 g, 20 mmol) in Et$_2$O (40 mL) was cooled to −20° C. and BuLi (8 mL 2.5N in hexane, 20 mmol) was added dropwise. Suspension obtained was stirred 1 h at room temperature, cooled again to −20° C., and ZrCl$_4$(THF)$_2$ (3.77 g, 10 mmol) was added. After 16 h of stirring, the precipitate was filtered off, dissolved in dichloromethane, solution was filtered and solvent was evaporated. Residue was washed with Et$_2$O, pentane and dried in vacuo giving 0.6 g of product as pure form. Filtrate was concentrated and 1.3 g of complex was obtained as mixture of isomers (1:1 ratio). (total yield 38%).

$^1$H NMR (CDCl$_3$): δ (for pure form) 6.51 (s, 2H); 6.37 (s, 2H); 6.32 (s, 2H); 6.05 (s, 2H); 5.83 (s, 2H); 2.40 (s, 6H); 2.07 (s, 6H).

Complex 54:

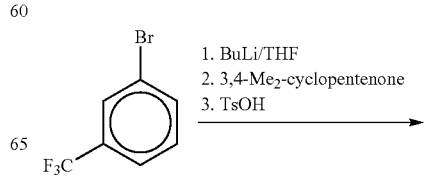

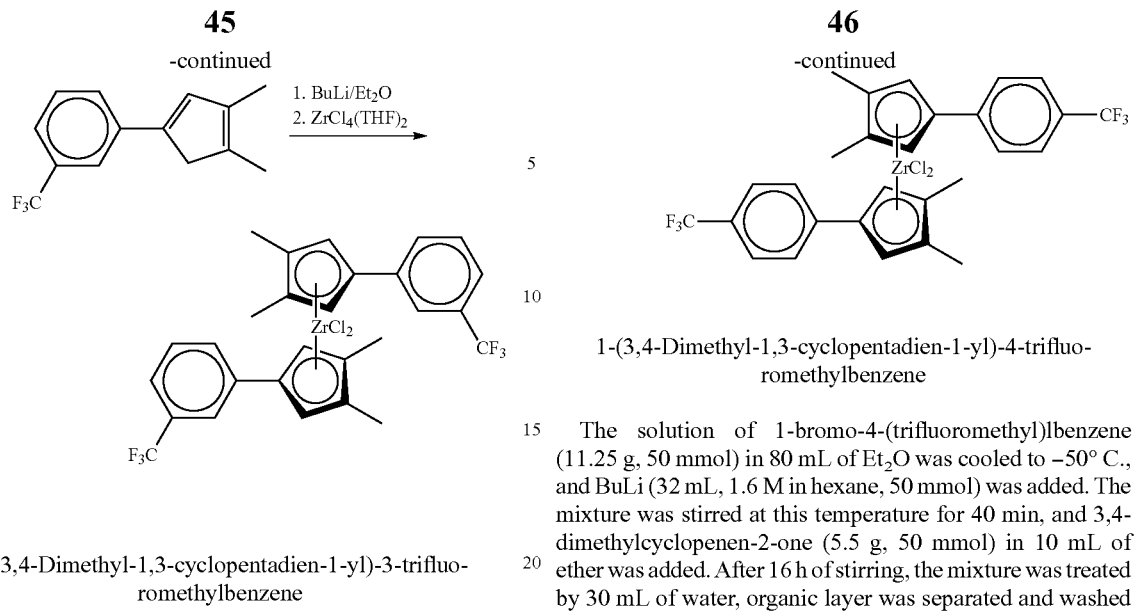

1-(3,4-Dimethyl-1,3-cyclopentadien-1-yl)-3-trifluoromethylbenzene

The solution of 1-bromo-3-(trifluoromethyl)lbenzene (22.5 g, 50 mmol) in 150 mL of Et$_2$O was cooled to −70° C., and BuLi (63 mL, 1.6 M in hexane, 100 mmol) was added. The mixture was stirred at this temperature for 2 h, 3,4-dimethylcyclopenen-2-one (11 g, 100 mmol) in 50 mL of ether was added, the mixture was stirred overnight, and treated by 30 mL of water. Organic layer was separated and washed by brine. TsOH (0.5 g) was added, and the mixture was refluxed for 3 min. After cooling the mixture was washed by 5% NaHCO$_3$, brine, dried over MgSO$_4$, solvent was evaporated and residue was distilled in vacuo, (b.p. 95-97° C./1 torr) yielding 14 g (59%) of the product.

$^1$H NMR (CDCl$_3$): δ 7.66 (br.s, 1H); 7.57 (m, 1H); 7.37 (m, 2H), 6.74 (br.s, 1H); 3.26 (s, 2H); 1.99 (s, 3H); 1.91 (d, 3H).

The solution of 1-(3,4-dimethyl-1,3-cyclopentadien-1-yl)-3-(trifluoromethyl)benzene (4.76 g, 20 mmol) in Et$_2$O (40 mL) was cooled to −30° C., and BuLi (12.5 mL, 1.6 M in hexane, 20 mmol) was added dropwise. The mixture was stirred 2 h at room temperature, cooled again to −30° C., and ZrCl$_4$(THF)$_2$ (3.77 g, 10 mmol) was added. After 16 h of stirring, precipitate was filtered off, dissolved in dichloromethane, solution was filtered and evaporated. Residue was washed with pentane and dried in vacuo. The yield was 4 g (63%).

$^1$H NMR (CDCl$_3$): δ 7.65 (s, 2H); 7.56 (m, 6H); 6.21 (s, 4H); 1.81 (s, 12H).

Complex 55

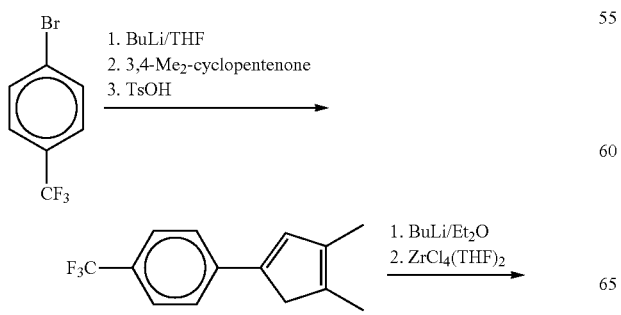

1-(3,4-Dimethyl-1,3-cyclopentadien-1-yl)-4-trifluoromethylbenzene

The solution of 1-bromo-4-(trifluoromethyl)lbenzene (11.25 g, 50 mmol) in 80 mL of Et$_2$O was cooled to −50° C., and BuLi (32 mL, 1.6 M in hexane, 50 mmol) was added. The mixture was stirred at this temperature for 40 min, and 3,4-dimethylcyclopenen-2-one (5.5 g, 50 mmol) in 10 mL of ether was added. After 16 h of stirring, the mixture was treated by 30 mL of water, organic layer was separated and washed by brine. TsOH (0.5 g) was added, and the mixture was refluxed for 1 min. After cooling the mixture was washed by 5% NaHCO$_3$, brine, dried over MgSO$_4$, solvent was evaporated and the residue was recrystallized from methanol, yielding 8.5 g (71.4%) of the product.

$^1$H NMR (CDCl$_3$): δ 7.56 (m, 4H); 6.84 (s, 1H); 3.33 (s, 2H); 2.06 (s, 3H); 1.97 (s, 3H).

The solution of 1-(3,4-dimethyl-1,3-cyclopentadien-1-yl)-4-(trifluoromethyl)benzene (4.76 g, 20 mmol) in Et$_2$O (40 mL) was cooled to −30° C., and BuLi (12.5 mL, 1.6 M in hexane, 20 mmol) was added dropwise. Mixture was stirred 2 h at room temperature, cooled again to −30° C., and ZrCl$_4$(THF)$_2$ (3.77 g, 10 mmol) was added. After 16 h of stirring, precipitate was filtered off and extracted by hot benzene. Solvent was evaporated, and the residue was washed by pentane and dried in vacuo. The yield was 3.1 g (48%).

$^1$H NMR (CDCl$_3$): δ 7.70 (d, 4H); 7.55 (d, 4H); 6.34 (s, 4H); 1.84 (s, 12H).

Complex 56:

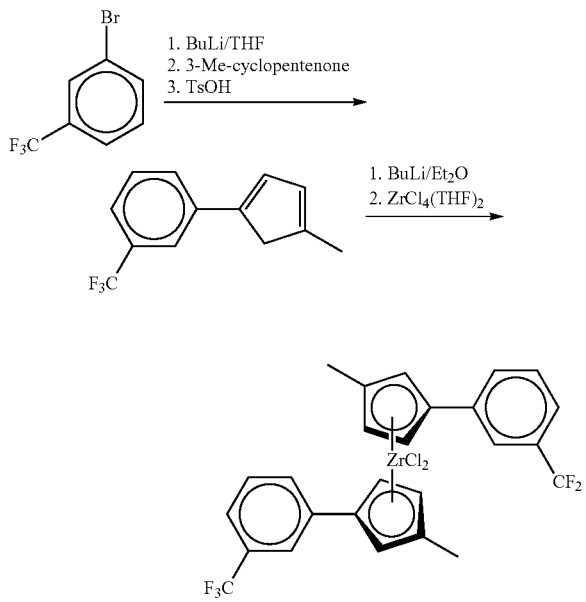

1-(4-Methylcyclopenta-1,4-dien-1-yl)-3-(trifluoromethyl)benzene

The solution of 1-bromo-3-(trifluoromethyl)benzene (22.5 g, 100 mmol) in 200 mL of Et$_2$O was cooled to −50° C., and BuLi (63 mL, 1.6 M in hexane, 100 mmol) was added. The mixture was stirred at this temperature for 1 h. The solution of 3-methylcyclopenen-2-one (9.6 g, 100 mmol) in 20 mL of ether was added and mixture was stirred overnight. Mixture was treated by 20 mL of water, organic layer was separated and washed by brine. TsOH (0.5 g) was added, and the mixture was refluxed for 1 min. After cooling the mixture was washed by 5% NaHCO$_3$, brine, dried over MgSO$_4$, solvent was removed, and the residue was recrystallized from methanol, yielding 14.6 g (65%) of the product.

$^1$H NMR (CDCl$_3$): δ 7.81-7.39 (group m, 4H, Aryl); 6.85 (bs); 6.55 (bs); 6.22 (bs); 6.08 (bs) {2H, —CH=}; 3.36 (bs); 3.29 (bs); 3.12 (bs) {2H, —CH$_2$—}; 2.16 (m), 2.14 (m); 2.07 (m) {3H, —CH$_3$}.

The solution of 1-(4-methyl-1,4-cyclopentadien-1-yl)-3-(trifluoromethyl)benzene (4.5 g, 20 mmol) in Et$_2$O (40 mL) was cooled to −30° C., and BuLi (12.5 mL, 1.6 M in hexane, 20 mmol) was added dropwise. Mixture was stirred for 2 h at room temperature, cooled to 0° C., and ZrCl$_4$(THF)$_2$ (3.7 g, 10 mmol) was added. After 16 h of stirring, the reaction mixture was filtered, filtrate was evaporated. Liquid residue was treated with pentane and was stated for 2 days. Yellow precipitate was filtered off and dried in vacuo. The yield was 2 g (33%).

$^1$H NMR (CDCl$_3$): δ 7.61 (m, 4H); 7.47 (m, 4H); 6.58 (m, 2H); 6.44 (m, 2H); 5.94 (m, 2H); 2.18 (s, 6H).

Complex 57 (57a—minor isomer, 57b—major isomer)

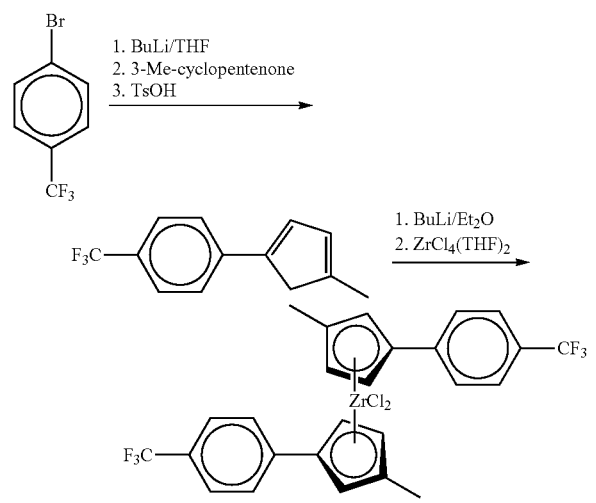

1-(4-Methylcyclopenta-1,4-dien-1-yl)-4-(trifluoromethyl)benzene

The solution of 1-bromo-4-(trifluoromethyl)benzene (13.8 g, 61 mmol) in 100 mL of Et$_2$O was cooled to −50° C., and BuLi (38 mL, 1.6 M in hexane, 61 mmol) was added. The mixture was stirred at this temperature for 1 h. The solution of 3-methylcyclopenen-2-one (5.8 g, 61 mmol) in 10 mL of ether was added and mixture was stirred overnight. The mixture was treated by 20 mL of water, organic layer was separated and washed by brine. TsOH (0.5 g) was added, and the mixture was refluxed for 1 min. After cooling the mixture was washed by 5% NaHCO$_3$, brine, dried over MgSO$_4$, solvent was removed, and the residue was recrystallized from methanol, yielding 4.3 g of product (32%).

$^1$H NMR (CDCl$_3$): δ 7.62-7.52 (group m, 4H, Aryl); 6.86 (bs); 6.09 (bs) {2H, —CH=}; 3.35 (bs, 2H, —CH$_2$—); 2.05 (bs, 3H, —CH$_3$).

The solution of 1-(4-methyl-1,4-cyclopentadien-1-yl)-4-(trifluoromethyl)benzene (4.3 g, 19 mmol) in Et$_2$O (40 mL) was cooled to −30° C., and BuLi (12 mL, 1.6 M in hexane, 19 mmol) was added dropwise. Mixture was stirred 1 h at room temperature, cooled to 0° C., and ZrCl$_4$(THF)$_2$ (3.4 g, 9 mmol) was added. After 16 h of stirring, reaction mixture was filtered, precipitate was washed with ether, filtrate was evaporated, residue was washed with pentane, yielding 2.2 g of complex as mixture of isomers, 57a and 57b (57b is the main isomer). Insoluble residue at filter was treated with dichloromethane, precipitate of LiCl was separated by centrifuge, solvent was evaporated, residue was washed with ether yielding 1.5 g of complex 57 (containing 57a and 57b).

Complex 57b $^1$H NMR (CDCl$_3$): δ 7.62 (d, 4H); 7.49 (d, 4H); 6.54 (m, 2H); 6.48 (m, 2H); 5.89 (m, 2H); 2.15 (s, 6H).

Complex 57a $^1$H NMR (CDCl$_3$): δ 7.61 (d, 4H); 7.49 (d, 4H); 6.58 (m, 2H); 6.44 (m, 2H); 5.94 (m, 2H); 2.18 (s, 6H).

Complex 58:

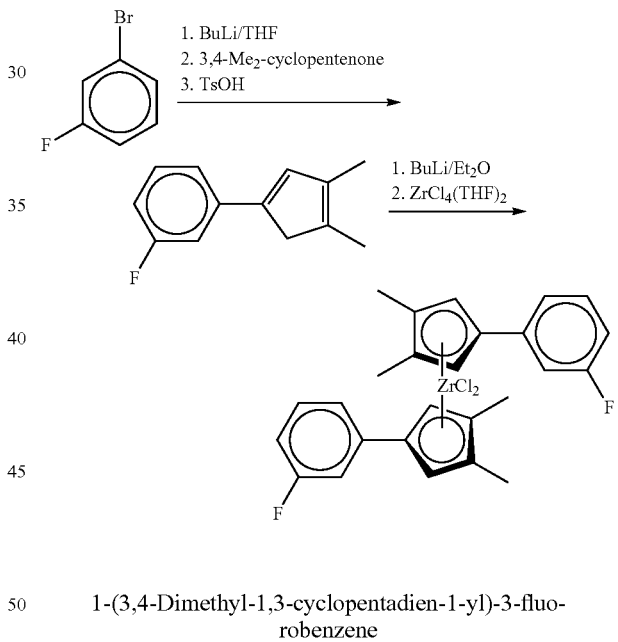

1-(3,4-Dimethyl-1,3-cyclopentadien-1-yl)-3-fluorobenzene

The solution of 1-bromo-3-fluorobenzene (12 g, 70 mol) in 100 mL of Et$_2$O was cooled to −50° C., and BuLi (44 mL, 1.6 M in hexane, 70 mmol) was added. The mixture was stirred at this temperature for 1 h and warmed to 0° C. The solution of 3,4-dimethylcyclopenen-2-one (7.7 g, 70 mmol) in 10 mL of ether was added, the mixture was stirred overnight, and treated by 30 mL of water. Organic layer was separated, washed by brine and the solvent was removed. Benzene (50 mL) and TsOH (0.5 g) were added, and the mixture was refluxed for 1 min. After cooling the mixture was washed by 5% NaHCO$_3$, brine, dried over MgSO$_4$, filtered through silica gel. Solvent was removed, and the residue was recrystallized from methanol, yielding 6.3 g of product (48%).

$^1$H NMR (CDCl$_3$): δ 7.40 (m, 2H); 6.99 (m, 2H); 6.59 (s, 1H); 3.24 (s, 2H); 1.99 (s, 3H); 1.91 (s, 3H).

The solution of 1-(3,4-dimethyl-1,3-cyclopentadien-1-yl)-3-fluorobenzene (5 g, 26 mmol) in Et$_2$O (50 mL) was cooled to −30° C., and BuLi (16.5 mL, 1.6 M in hexane, 26 mmol) was added dropwise. The mixture was stirred 2 h at room temperature, cooled to 0° C., and ZrCl$_4$(THF)$_2$ (4.9 g, 13 mmol) was added. After 16 h of stirring, reaction mixture was filtered, solid residue was washed with ether and the solvent was evaporated. Residue was extracted by 50 mL of benzene-hexane mixture (1:1), and the yellow precipitate was filtered and dried in vacuo. The yield was 4 g (58%).

$^1$H NMR (CDCl$_3$): δ 7.43 (m, 4H); 7.15 (m, 3H); 6.21 (m, 4H); 1.80 (s, 12H).

Complex 59:

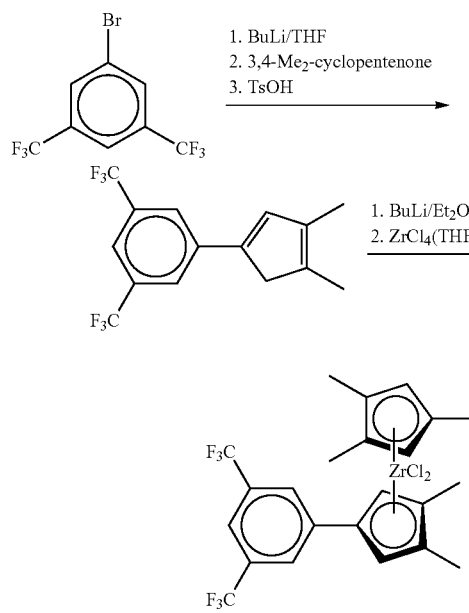

1-(3,4-Dimethyl-1,3-cyclopentadien-1-yl)-3,5-bis(trifluoromethyl)benzene

The solution of 1-bromo-3,5-bis(trifluoromethyl)benzene (10 g, 34 mmol) in 50 mL of Et$_2$O was cooled to −70° C., and BuLi (22 mL, 1.6 M in hexane, 35 mmol) was added. The mixture was stirred at this temperature for 1 h, 3,4-dimethyl-cyclopenen-2-one (3.3 g, 30 mmol) in 10 mL of ether was added, the mixture was stirred overnight, and treated by 20 mL of water. Organic layer was separated and washed by brine. TsOH (0.5 g) was added, and the mixture was refluxed for 3 min. After cooling the mixture was washed by 5% NaHCO$_3$, brine, dried over MgSO$_4$, solvent was evaporated and the residue was recrystallized from methanol, yielding 4.7 g (63%) of the product.

$^1$H NMR (CDCl$_3$): δ 7.81 (s, 2H); 3.61 (s, 1H); 6.87 (s, 1H); 3.32 (s, 2H); 2.03 (s, 3H); 1.94 (s, 3H).

The solution of 1-(3,4-dimethyl-1,3-cyclopentadien-1-yl)-3,5-bis(trifluoromethyl)benzene (2.4 g, 8 mmol) in Et$_2$O (30 mL) was cooled to −30° C., and BuLi (5 mL, 1.6 M in hexane, 8 mmol) was added dropwise. The mixture was stirred 2 h at room temperature, cooled to 0° C., and ZrCl$_4$(THF)$_2$ (1.5 g, 4 mmol) was added. After 16 h of stirring, the mixture was filtered, filtrate was evaporated. Residue was treated with pentane, yellow precipitate was filtered off and dried in vacuo. The yield was 0.9 g (29%).

$^1$H NMR (CDCl$_3$): δ 7.77 (br s, 6H); 6.25 (s, 4H); 1.86 (s, 12H).

Complex 62

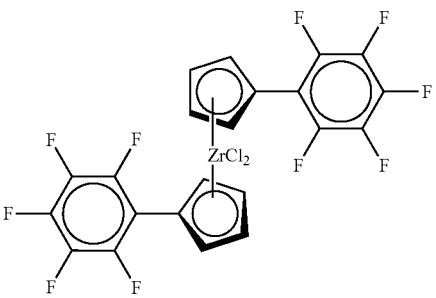

Complex 62 was synthesized as described in *Organometallics*, 1996, 15, 5287.

Complex 60:

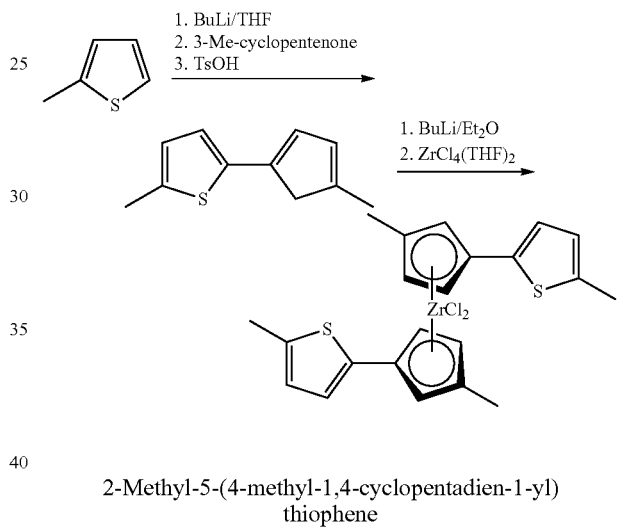

2-Methyl-5-(4-methyl-1,4-cyclopentadien-1-yl)thiophene

The solution of 2-methylthiophene (9.8 g, 100 mmol) in 100 mL of Et$_2$O was cooled to −30° C., and BuLi (50 mL 2.5N in hexane, 80 mmol) was added. The mixture was stirred at this temperature for 40 min, warmed to 0° C., and 3-methylcyclopenen-2-one (7.7 g, 80 mmol) in 10 mL of ether was added. After 16 h of stirring, the mixture was treated by 30 mL of water, organic layer was separated, washed by brine and concentrated to 100 mL. TsOH (0.5 g) was added, and the mixture was refluxed for 1 min. After cooling the mixture was washed by 5% NaHCO$_3$, brine, dried over MgSO$_4$, solvent was evaporated and the residue was distilled in vacuo, yielding 5.5 g of product as a mixture of 3 isomers (39%, b.p. 90-94° C./1 torr).

$^1$H NMR (CDCl$_3$): δ 6.83 (gr. signals, 1H); 6.64 (m, 1H); 6.45 (gr. signals, 1H); 6.07 (gr. signals, 1H); 3.21 (gr. signals, 2H); 2.49 (gr. signals, 3H); 2.08 (gr. signals, 3H).

The solution of 2-(3,4-dimethyl-1,3-cyclopentadien-1-yl)-5-methylthiophene (3.52 g, 20 mmol) in Et$_2$O (30 mL) was cooled to −20° C., and BuLi (8 mL 2.5N in hexane, 20 mmol) was added dropwise. Suspension obtained was stirred 2 h at room temperature, cooled again to −20° C., and ZrCl$_4$(THF)$_2$ (3.77 g, 10 mmol) was added. After 16 h of stirring the precipitate was filtered, dissolved in dichloromethane, solution was filtered and solvent was evaporated. The residue was washed with pentane and dried in vacuo giving 1.6 g (31%) of the product as a mixture of isomers (1:2 ratio).

$^1$H NMR (CDCl$_3$): δ 6.92 (m, 2H); 6.70 (m, 2H); 6.36 (m, 2H); 6.33 (m, 2H); 5.76 (m, 2H); 2.53 (2 s, 6H); 2.14 and 2.09 (2 s, 6H).

Complex 66:

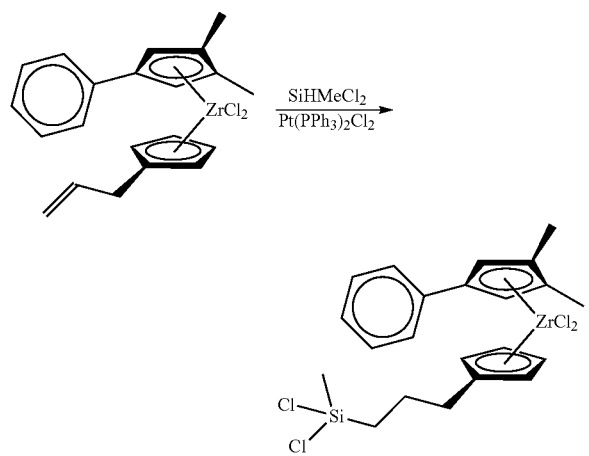

Pt(PPh$_3$)$_2$Cl$_2$ (35 mg, 44 mmol) was added to solution of complex 342 (0.96 g, 2.2 mmol) and SiHMeCl$_2$ (0.51 g, 4.4 mmol) in toluene (20 mL). The mixture was heated with stirring at 60° C. for 6 h, and 16 h at room temperature. The solvent was removed under reduced pressure, and the residue was recrystallized from pentane yielding 0.56 g (59%) of the product.

$^1$H NMR (CDCl$_3$): δ 7.51 (d, 2H); 7.44 (t, 2H); 7.30 (t, 1H); 6.61 (s, 2H); 5.95 (bs, 2H); 5.90 (bs, 2H); 2.54 (t, 4H); 1.63 (m, 4H); 1.04 (m, 4H); 0.74 (s, 6H).

$^{13}$C NMR (CDCl$_3$): δ 133.87; 133.49; 129.15; 128.40; 127.59; 125.13; 121.90; 117.21; 114.10; 114.07; 32.42; 23.57; 21.24; 13.84; 5.13.

Example 2

Metallocene Catalytic Activity

All metal complexes were tested for ethylene-butene co-polymerization in identical, commercially relevant slurry polymerization conditions in a standard MAO-activated (Al/M=100) and silica-supported catalyst recipe, prepared using the pore filling (incipient wetness) method described below.

Preparation of supported catalysts: According to a general recipe, 5.05×10$^{-5}$ moles of complex were dissolved in 1.2 mL of 30% MAO, corresponding to Al/metal ratio of 100. After 30 minutes stirring at ambient temperature, the resulting solution was slowly and evenly added drop wise to a stirred bed of Davison 948 silica, calcined for 6 h at 600° C. After 15 minutes of further stirring, the catalyst was vacuum-dried for 15 minutes. The catalysts were usually tested within 24 hours of preparation.

Catalyst Testing: To a dry 2 L stainless steel autoclave charged with 1 L of iso-butane, 100 mL of butene-1 and 2 mL of 1M TIBAL solution and saturated at 70° C. with 15.5 bar (225 psi) partial pressure with ethylene, a catalyst charge (0.05 g to 0.1 g) was injected in iso-butane to start the polymerization. The ethylene was supplied on demand in order to maintain the reactor pressure. In runs with H$_2$, the hydrogen gas was dosed in before the run from a 7 mL or a 300 mL H$_2$ vessel pressurized to the initial pressure of 600 psi and quantified by a specific pressure drop (e.g., 20 Δ psi). After 1 hour, the polymerization was terminated by venting the reactor. The dried polymer samples were analyzed by GPC, FT-IR and rheological tests. See Table 2 below.

TABLE 2

| R# | A, g/g/h | A, kg/mol/h | Mw | Mw/Mn | Br/1000 | Eta 100 | Er |
|---|---|---|---|---|---|---|---|
| Benchmarks | | | | | | | |
| 1 | 1,195 | 48,235 | 197,000 | 2.4 | 23 | 57,400 | 0.74 |
| 2 | 1,478 | 55,992 | 197,755 | 2.84 | 24.4 | 50,200 | 1.9 |
| 3 | 433 | 32,994 | 329,407 | 3.32 | 27.6 | 76,600 | 0.95 |
| 4 | 423 | 14,887 | 316,662 | 3.2 | 26.2 | 62,900 | 0.76 |
| 5 | 482 | 16,641 | 279,000 | 3.2 | — | 56,100 | 0.83 |
| (R-Alk-Cp)$_2$ | | | | | | | |
| 6 | 1,640 | 71,820 | 101,283 | 2.83 | 25 | 16,100 | 0.27 |
| 7 | 437 | 20,570 | 149,315 | 3.71 | 17.8 | 26,400 | nr |
| 8 | 49 | 1,871 | 54,200 | 4.43 | 24 | 3,000 | 1.77 |
| 9 | 1,325 | 45,263 | 234,000 | 2.71 | 17.3 | 66,800 | 0.83 |
| 10 | 3,145 | 115,697 | 116,359 | 2.34 | 22.7 | 22,100 | 0.35 |
| 11 | 1,439 | 49,708 | 116,000 | 2.49 | 18.9 | 20,700 | nr |
| 12 | 1,976 | 77,169 | 107,000 | 2.4 | 27.4 | 18,700 | 0.27 |
| 13 | 2,139 | 86,030 | 107,615 | 2.26 | 26.6 | 17,600 | 0.19 |
| 14 | 2,315 | 64,356 | 128,000 | 2.53 | 21 | 25,000 | 0.44 |
| 15 | 881 | 41,601 | 91,400 | 3.09 | 19 | 10,600 | nr |
| 16 | 50 | 1,857 | 185,011 | 5.9 | — | — | — |
| 17 | 399 | 12,475 | 384,000 | 3.11 | 25.1 | 81,900 | 0.54 |
| 18 | 174 | 6,370 | 382,000 | 3.56 | 26.7 | 75,500 | 0.77 |
| (R-Alk-Cp)(Ind) | | | | | | | |
| 19 | 1,749 | 84,340 | 172,316 | 2.83 | 18.3 | 36,100 | 2.24 |
| 20 | 279 | 10,621 | 168,490 | 5.09 | 27.2 | 23,500 | 1 |
| 21 | 2,110 | 75,756 | 145,550 | 2.7 | 18.4 | 32,800 | 0.46 |
| 22 | 106 | 7,015 | 223,954 | 5.58 | 17 | 29,300 | 5.13 |
| 23 | 2,347 | 74,973 | 118,000 | 2.66 | 20.3 | 20,600 | 0.27 |
| 24 | 2,669 | 120,860 | 128,000 | 2.49 | 18.6 | 23,400 | nr |
| 25 | 575 | 19,609 | 167,871 | 3.66 | 15.4 | 36,900 | 0.58 |
| 26 | 0 | 0 | — | n/a | n/a | — | n/a |

TABLE 2-continued

| R# | A, g/g/h | A, kg/mol/h | Mw | Mw/Mn | Br/1000 | Eta 100 | Er |
|---|---|---|---|---|---|---|---|
| (Ind)₂ | | | | | | | |
| 27 | 604 | 18,219 | 142,929 | 2.93 | 14.9 | 29,500 | 0.67 |
| 28 | 1,021 | 33,284 | 118,207 | 3.64 | 10 | 16,700 | 0.42 |
| 29 | 267 | | 182,000 | 8.9 | 18.4 | 27,600 | 2.61 |
| 30 | 1,200 | 57,448 | 235,265 | 3.5 | 19.2 | 41,100 | 2.25 |
| 31 | 232 | 8,914 | 336,000 | 6.25 | 19.9 | 72,500 | 0.52 |
| 32 | 0 | 0 | — | n/a | n/a | — | n/a |
| 33 | 450 | 16,452 | 164,407 | 2.04 | 8.2 | 29,500 | n/r |
| 34 | 21 | 611 | 181,380 | 2.97 | — | — | n/a |
| 35 | 64 | 4,579 | 263,427 | 4.29 | 15.9 | 25,900 | 6.95 |
| 36 | 56 | 4,398 | 289,502 | 5.14 | 17.9 | 37,300 | 6.63 |
| 37 | 1,073 | 35,342 | 148,000 | 3.47 | 20.1 | 31,100 | 0.59 |
| 38 | 876 | 34,689 | 157,000 | 3.65 | 18.3 | 31,500 | 0.54 |
| (Ar-Cp)₂ | | | | | | | |
| 39 | 1,095 | 33,719 | 455,734 | 2.76 | 26.4 | 94,800 | |
| 40 | 336 | 13,615 | 511,856 | 2.5 | 28.3 | 95,000 | nr |
| 41 | 1,118 | 42,452 | 526,720 | 3.12 | 17.8 | 92,000 | nr |
| 42 | 61 | 2,340 | 505,557 | 3.13 | 2.6 | 86,000 | nr |
| 43 | 526 | 21,417 | 318,420 | 2.79 | 18 | 71,700 | nr |
| 44 | 938 | 41,005 | not sol | — | 19.1 | 80,300 | nr |
| 45 | 1,012 | 30,206 | 354,000 | 3.15 | 19.3 | 84,400 | nr |
| 46 | 689 | 27,821 | 549,000 | 4.13 | 14.3 | 101,000 | nr |
| 47 | 79 | 3,790 | 117,000 | 3.93 | 8 | — | — |
| 48 | 1,227 | 34,594 | not sol | — | 17.3 | 78,200 | nr |
| 49 | 445 | 15,654 | 357,700 | 3.4 | 14.6 | 71,900 | nr |
| 50 | 1,591 | 65,481 | 396,341 | 2.74 | 12.4 | 71,200 | nr |
| 51 | 487 | 13,899 | 532,000 | 5.87 | 22.3 | 96,100 | — |
| 52 | 2,182 | 64,861 | 340,000 | 2.83 | 23.6 | 66,200 | 22.4 |
| 53 | 2,100 | 60,589 | 294,000 | 2.47 | 14.8 | no melt | — |
| 54 | 1,647 | 52,076 | 545,000 | 3.82 | 18.1 | 96,000 | nr |
| 55 | 864 | 29,136 | 469,000 | 2.62 | 16 | 101,000 | nr |
| 56 | 1,623 | 59,713 | 426,000 | 2.59 | 20 | 76,000 | — |
| 57 | 991 | 36,576 | 359,000 | 2.73 | 18.5 | 79,600 | — |
| 58 | 250 | 6,441 | 419,000 | 2.97 | — | 91,400 | — |
| 59 | 882 | 31,673 | 743,000 | 2.94 | 18.9 | 95,800 | nr |
| 60 | 1,680 | 51,084 | 310,000 | 2.8 | 17.1 | 75,400 | 33.8 |
| 61 | 366 | 11,214 | 366,000 | 2.57 | 17.2 | 84,100 | 51.3 |
| 62 | 0 | 0 | — | — | — | — | — |
| (R-Alk-Cp)(Ar-Cp) | | | | | | | |
| 63 | 158 | 5,160 | 202,801 | 3.24 | 16 | 46,100 | 3.46 |
| 64 | 1,926 | 55,265 | 158,000 | 2.5 | 20 | 35,000 | 0.64 |
| 65 | 1,789 | 64,438 | 167,000 | 2.55 | 17.7 | 42,500 | 1.32 |
| 66 | 2,408 | 77,486 | 192,000 | 2.48 | 16 | 49,600 | 2.31 |
| (Ind)(Ar-Cp) | | | | | | | |
| 67 | 2,003 | 75,596 | 181,000 | 2.56 | 12.3 | 45,000 | 0.66 |
| 68 | 1,149 | 43,022 | 197,000 | 2.74 | 14.8 | 52,200 | 2.93 |
| 69 | 57 | 2,066 | 169,000 | 3.75 | 11.8 | | |
| 70 | 1,925 | 77,672 | 149,015 | 2.62 | 21.9 | 36,300 | 1.54 |

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of the ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A catalyst composition comprising:
(A) a metallocene complex having the formula:

(Formula VII)

wherein $L_1$ and $L_2$ are each independently a ligand of the formula:

(Formula VIII)

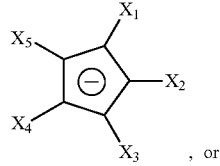

, or

-continued

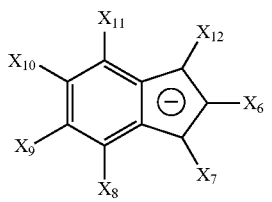
(Formula IX)

wherein:
- $X_1$ is $CH_2$—$CH_2$—$CH_2$—$SiCH_3Cl_2$, —$CH_2$—$CH_2$—$CH_2$—$SiCl_3$, or —$CH_2$—$CH_2$—$CH_2$—$CH_2$—$CH_2$—$SiCH_3Cl_2$, or a substituted version of any of these groups;
- $X_2$, $X_3$, $X_4$, $X_5$, $X_6$, $X_7$, $X_8$, $X_{10}$, and $X_{11}$ are each independently hydrogen, alkyl$_{C\leq8}$, alkenyl$_{C\leq8}$, alkynyl$_{C\leq8}$, aryl$_{C\leq12}$, aralkyl$_{C\leq12}$, heterocycloalkyl$_{C\leq12}$, heteroaryl$_{C\leq12}$;
- $X_9$ is hydrogen, alkyl$_{C\leq8}$, alkenyl$_{C\leq6}$, —O—Si—$R^1R^2R^3$ or a substituted version of either of these groups, wherein $R^1$, $R^2$ and $R^3$ are independently selected from alkyl$_{C\leq6}$, or alkenyl$_{C\leq6}$, or a substituted version of either of these groups;
- $X_{12}$ is hydrogen, alkyl$_{C\leq8}$, or alkenyl$_{C\leq6}$ or a substituted version of either of these groups; M is Ti, Zr, or Hf; and
- $Y_1$ and $Y_2$ are each independently a hydride, halide, carboxylate, phosphine, amine, alkylamino, alkenylamino, alkynylamino, arylamino, aralkylamino, alkoxylate, alkenyloxylate, alkynyloxylate, aryloxylate, or aralkyloxylate.

2. The catalyst composition of claim 1, wherein the catalyst composition comprises:
(B) an activator.

3. The catalyst composition of claim 1, wherein the catalyst composition is supported on a solid support.

4. The catalyst composition of claim 3, wherein the solid support is an inorganic oxide.

5. The catalyst composition of claim 4, wherein the inorganic oxide is silica, alumina, magnesium oxide, titanium oxide or a combination thereof.

6. The catalyst composition of claim 1, wherein $X_1$ is —$CH_2$—$CH_2$—$CH_2$—$SiCH_3Cl_2$, —$CH_2$—$CH_2$—$CH_2$—$SiCl_3$, —$CH_2$—$CH_2$—$CH_2$—$CH_2$—$CH_2$—$SiCH_3Cl_2$.

7. The catalyst composition of claim 6, wherein $X_2$, $X_3$, $X_4$, and $X_5$ are hydrogen.

8. The catalyst composition of claim 1, wherein $X_6$, $X_7$, $X_8$, $X_{10}$, and $X_{11}$ are each independently hydrogen or methyl.

9. The catalyst composition of claim 1, wherein $X_9$ is hydrogen, —O—Si—$R^1R^2R^3$, wherein $R^1$, $R^2$ and $R^3$ are independently selected from methyl, tert-butyl, —$CH_2$—$CH_2$—$CH_2$—$CH_2$—$CH$=$CH_2$.

10. The catalyst composition of claim 1, wherein $X_{12}$ is hydrogen or —$CH_2$—$CH_2$—$CH_2$—$SiCH_3Cl_2$.

11. The catalyst composition of claim 1, wherein $L_1$ and $L_2$ are each independently selected from:

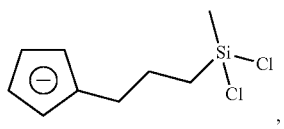
,

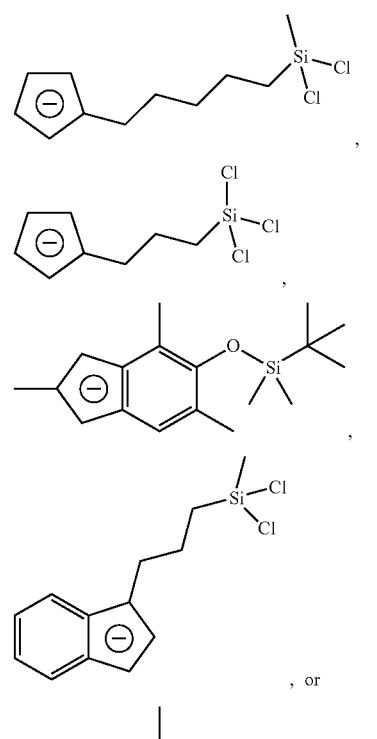

12. The catalyst composition of claim 1, wherein $Y_1$ and $Y_2$ are each independently chloride.

13. The catalyst composition of claim 1, wherein the metallocene catalyst has the formula:

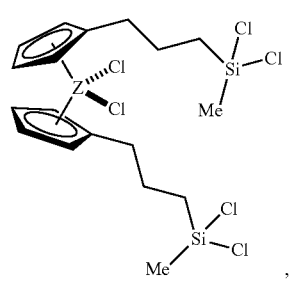

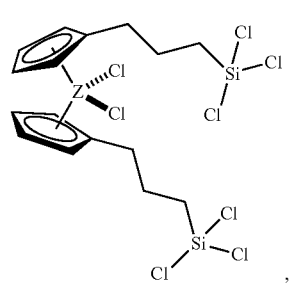
,

57
-continued
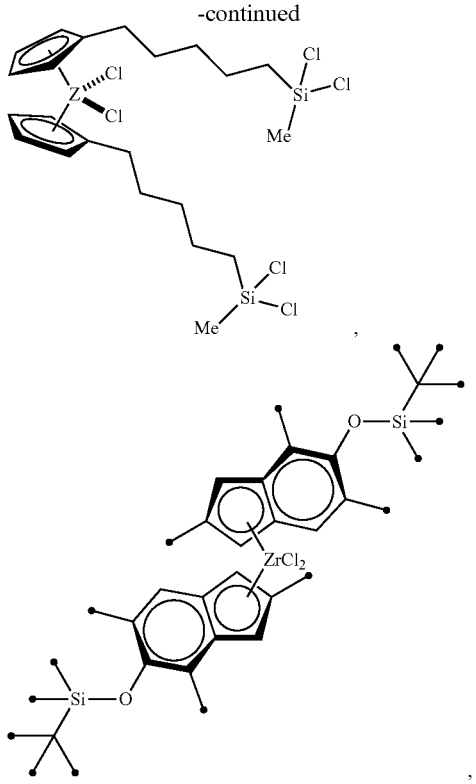
,
58
-continued
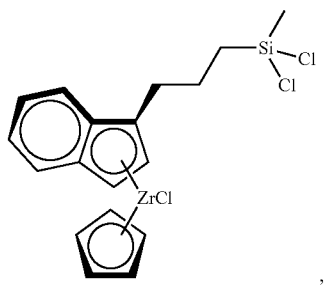
, or
* * * * *